(12) United States Patent
Han et al.

(10) Patent No.: US 7,977,366 B2
(45) Date of Patent: Jul. 12, 2011

(54) TREATING AN INFLAMMATORY DISORDER OR INHIBITING RESPIRATORY BURST IN ADHERENT NEUTROPHILS WITH CHEMICAL INHIBITORS OF NEUTROPHIL ACTIVATION

(75) Inventors: Hyunsil Han, New York, NY (US); Gang Lin, New York, NY (US); Carl Nathan, Larchmont, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 1143 days.

(21) Appl. No.: 10/575,683

(22) PCT Filed: Oct. 14, 2004

(86) PCT No.: PCT/US2004/033914
§ 371 (c)(1),
(2), (4) Date: Aug. 31, 2006

(87) PCT Pub. No.: WO2005/037213
PCT Pub. Date: Apr. 28, 2005

(65) Prior Publication Data
US 2007/0021448 A1  Jan. 25, 2007

Related U.S. Application Data

(60) Provisional application No. 60/510,843, filed on Oct. 14, 2003.

(51) Int. Cl.
*A61K 31/4709* (2006.01)
*A61K 31/41* (2006.01)
*A61P 37/00* (2006.01)

(52) U.S. Cl. .......... 514/396; 514/403; 514/468

(58) Field of Classification Search .......... 514/267, 514/367, 406, 314, 396, 403, 468
See application file for complete search history.

(56) References Cited

U.S. PATENT DOCUMENTS

| 5,462,946 | A | * | 10/1995 | Mitchell et al. .......... 514/315 |
| 5,475,017 | A | | 12/1995 | Wuest et al. |
| 2002/0119988 | A1 | | 8/2002 | Sneddon et al. |
| 2003/0073712 | A1 | | 4/2003 | Wang et al. |

FOREIGN PATENT DOCUMENTS

WO  WO 2003024446  * 3/2003

OTHER PUBLICATIONS

Ram et al."Thieno[2,3-d]pyrimidines as Potential Chemotherapeutic Agents. II.", J Het Chem, 1981, 18, 1227-1280.*
http://www.medilexicon.com/medicaldictionary.php?t=13063.*
Picciola et al., "Composti Eterociclici a Potenziale Attivita Antiinflammatoria Contenenti il Residuo di un Acido 4-Amminofenilalcanoico," *Farmaco* 39:371-378 (1984).

Short & Schoeb, "Synthesis and Structure of 5-Oxo-1-Phenylpyrazoline-3- and 4-Alkanoic Acids. Antiinflammatory Agents," *J. Heterocyclic Chem.* 6:723-728 (1969).
International Search Report for PCT/US04/33914 (May 26, 2006).
Written Opinion for PCT/US2004/033914 (May 26, 2006).
Han et al., "Critical Role of the Carboxyl Terminus of Proline-Rich Tyrosine Kinase (Pyk2) in the Activation of Human Neutrophils by Tumor Necrosis Factor: Separation of Signals for the Respiratory Burst and Degranulation," *J. Exp. Med.* 197(1):63-75 (2003).

(Continued)

*Primary Examiner* — Sreeni Padmanabhan
*Assistant Examiner* — Sahar Javanmard
(74) *Attorney, Agent, or Firm* — LeClairRyan

(57) ABSTRACT

The present invention relates to a method of treating an inflammatory disorder in a subject with an effective amount of compound having the general formula (I) as described in the present application, under conditions effective to treat the inflammatory disorder. The present invention also relates to a method of inhibiting respiratory burst in neutrophils without inhibiting degranulation in or bacterial killing by the neutrophils by contacting neutrophils with the compounds described above.

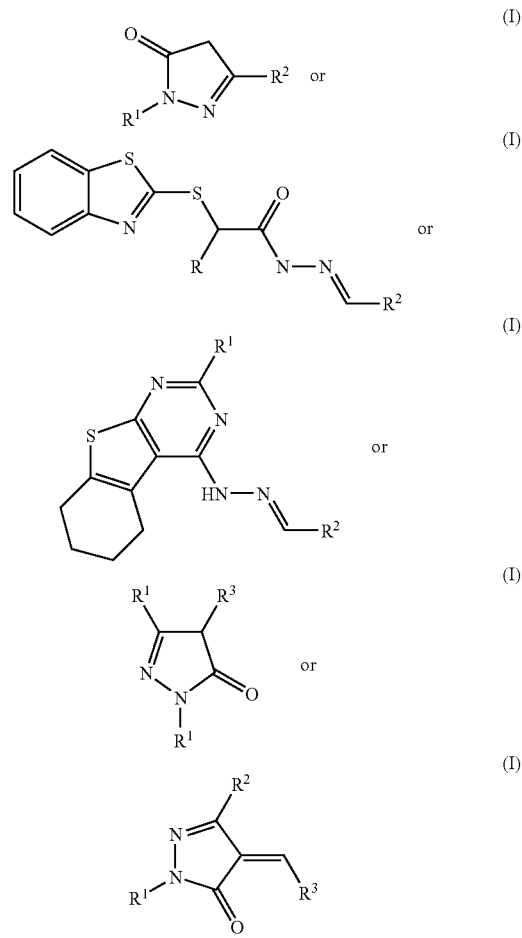

24 Claims, 22 Drawing Sheets

OTHER PUBLICATIONS

Han et al., "Chemical Inhibitors of TNF Signal Transduction in Human Neutrophils Point to Distinct Steps in Cell Activation," J. Leukoc. Biol. 79:147-154 (2006).

Han et al., "Calcium-Sensing Soluble Adenylyl Cyclase Mediates TNF Signal Transduction in Human Neutrophils," J. Exp. Med. 202(3):353-361 (2005).

Han, "Tumor Necrosis Factor Triggered Signaling Cascades in Adherent Human Neutrophils: Separation of Signals for the Respiratory Burst and Degranulation," Dissertation Presented to the Faculty of the Joan and Sanford I. Weill Graduate School of Biomedical Sciences of Cornell University (Indexed Feb. 2004).

Parsons, "Focal Adhesion Kinase: The First Ten Years," J. Cell Sci. 116:1409-1416 (2003).

Sadhu et al., "Essential Role of Phosphoinositide 3-Kinase Delta in Neutrophil Directional Movement," J. Immunol. 170:2647-2654 (2003).

Nathan, "Inflammation as a Flow of Information," Oral Presentation, Weill Medical College, Cornell University (Oct. 15, 2003).

* cited by examiner

Combinatorial compound library

- 15,000 compounds screened; collection growing
- Novel "drug like" molecules by Lipinski's "rule of 5"
- Based on 125 templates, 200 congeners each

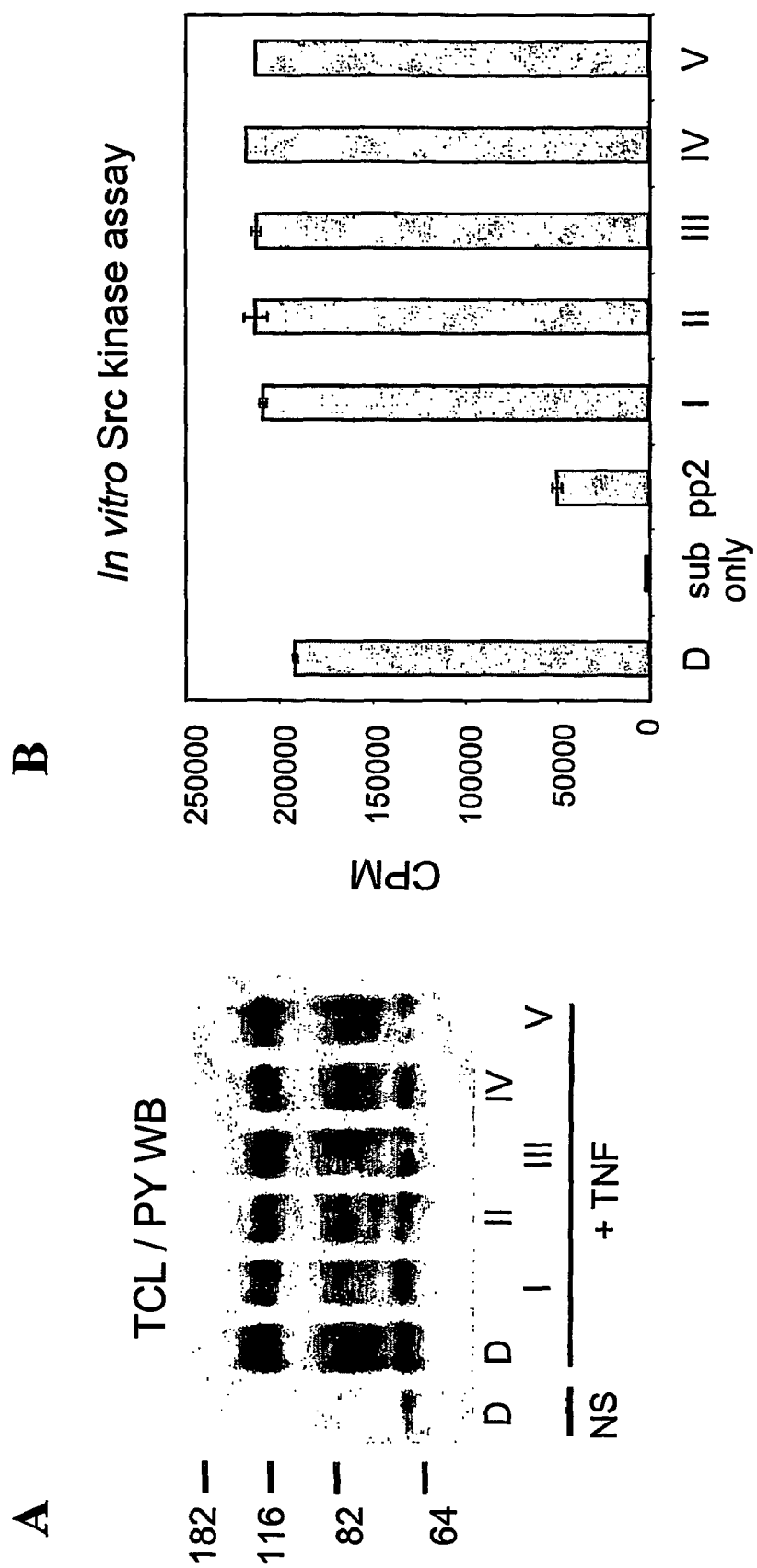
Figure 14A-B

TREATING AN INFLAMMATORY DISORDER OR INHIBITING RESPIRATORY BURST IN ADHERENT NEUTROPHILS WITH CHEMICAL INHIBITORS OF NEUTROPHIL ACTIVATION

This application claims the benefit of U.S. Provisional Patent Application Ser. No. 60/510,843, filed Oct. 14, 2003, which is hereby incorporated by reference in its entirety.

The subject matter of this application was made with support from the United States Government under The National Institutes of Health (NIH) grants ROI-A146382 and T32-A1 07621. The U.S. Government may have certain rights.

FIELD OF THE INVENTION

The present invention relates to methods of treating inflammatory disorders and inhibiting soluble effector-triggered respiratory burst triggered by bacteria in adherent neutrophils without inhibiting neutrophil degranulation in response to either soluble effectors or bacteria.

BACKGROUND OF THE INVENTION

Neutrophils are polymorphonuclear leukocytes (PMNs) of the blood that play a major role in almost all forms of acute inflammation and many forms of chronic inflammation, such as rheumatoid arthritis. When triggered, neutrophils secrete potent oxidants and proteases that contribute to inflammation but also help protect the host from infection. Neutrophils respond to soluble inflammatory mediators by migrating to the site of tissue injury and by ingesting and destroying invading pathogens and damaged tissue, leading, ultimately, to resolution and tissue repair. An inherent dilemma of anti-inflammatory therapy, the risk of impairing host defense, is particularly problematic with neutrophils.

To participate effectively in the inflammatory process, neutrophils must leave the bloodstream and migrate into the tissues. The initial step in this process is adherence to the vascular endothelium. Adherence of neutrophils to endothelium, their diapedesis from venules into tissues, and their release of peptides, proteases, and reactive oxygen intermediates underlie both their killing of bacteria and their damage to tissues.

Full activation of neutrophils by soluble host products requires a binary signal. One part of the signal consists of integrin ligation during adherence to extracellular matrix. Simultaneously, a factor such as tumor necrosis factor (TNF), lymphotoxin, C5a, formylated peptides, macrophage inflammatory protein (MIP-1), granulocyte-specific colony stimulating factor (G-CSF), or granulocyte-macrophage-specific colony stimulating factor (GM-CSF), must engage its receptor(s) on the neutrophil. Klebanoff et al., "Stimulation of Neutrophils by Tumor Necrosis Factor," *J. Immunol.* 136: 4220-4225 (1986); Nathan, "Neutrophil Activation on Biological Surfaces. Massive Secretion of Hydrogen Peroxide in Response to Products of Macrophages and Lymphocytes," *J. Clin. Invest.* 80:1550-1560 (1987); Wolpe et al., "Macrophages Secrete a Novel Heparin-Binding Protein with Inflammatory and Neutrophil Chemokinetic Properties," *J. Exp. Med.* 167:570-581 (1988); Nathan, "Respiratory Burst in Adherent Human Neutrophils: Triggering by Colony-Stimulating Factors CSF-GM and CSF-G," *Blood* 73:301-306 (1989). TNF has been studied extensively with respect to both the mechanisms by which it activates adherent neutrophils (Nathan C. F., "Neutrophil Activation on Biological Surfaces. Massive Secretion of Hydrogen Peroxide in Response to Products of Macrophages and Lymphocytes," *J. Clin. Invest.* 80:1550-1560 (1987); De La Harpe et al., "Adenosine Regulates the Respiratory Burst of Cytokine-Triggered Human Neutrophils Adherent to Biologic Surfaces," *J. Immunol.* 143: 596-602 (1989); Laudanna et al., "Tumor Necrosis Factor-Alpha/Cachectin Activates the $O_2^-$-Generating System of Human Neutrophils Independently of the Hydrolysis of Phosphoinositides and the Release of Arachidonic Acid," *Biochem. Biophys. Res. Commun.* 166:308-315 (1990); Nathan et al., "Tumor Necrosis Factor and CD11/CDI8 (beta 2) Integrins Act Synergistically to Lower cAMP in Human Neutrophils," *J. Cell Biol.* 111:2171-2181 (1990); Dri et al., "Effect of Biological Surfaces on Neutrophil $O_2$-Production and its Relationship to the CD11b/CDI8 Integrin-Dependent Adherence, *Int. J. Tissue React.* 13:193-201 (1991); Dapino et al., "Induction of Neutrophil Respiratory Burst by Tumour Necrosis Factor-Alpha; Priming Effect of Solid-Phase Fibronectin and Intervention of CD11b-CD18 Integrins," *Clin. Exp. Immunol* 94:533-538 (1993); Fuortes et al., "Adhesion-Dependent Protein Tyrosine Phosphorylation in Neutrophils Treated with Tumor Necrosis Factor," *J. Cell Biol.* 120: 777-784 (1993); Nathan et al., "Albumin inhibits Neutrophil Spreading and Hydrogen Peroxide Release by Blocking the Shedding of CD43 (Sialophorin, Leukosialin)," *J. Cell Biol.* 122:243-256 (1993); Liles et al., "Cross-Linking of CDI8 Primes Human Neutrophils for Activation of the Respiratory Burst in Response to Specific Stimuli: Implications for Adhesion-Dependent Physiological Responses in Neutrophils," *J. Leukoc. Biol.* 58:690-697 (1995); Richter et al., "TNF-Induced Superoxide Anion Production in Adherent Human Neutrophils Involves Both the p55 and p75 TNF Receptor," *J. Immunol.* 154:4142-4149 (1995); Puortes et al., "Ceramide Selectively Inhibits Early Events in the Response of Human Neutrophils to Tumor Necrosis Factor," *J. Leukoc. Biol.* 59:451-460 (1996); Lowell et al., "Deficiency of Src Family Kinases p59/61hck and p58c-fgr Results in Defective Adhesion-Dependent Neutrophil Functions," *J. Cell Biol.* 133:895-910 (1996)) and the benefit of its neutralization in inflammatory disorders such as rheumatoid arthritis (Feldmann, "Development of Anti-TNF Therapy for Rheumatoid Arthritis," *Nat. Rev. Immunol.* 2:364-371 (2002)); ankylosing spondylitis (Braun et al., "Treatment of Active Ankylosing Spondylitis with Infliximab: A Randomised Controlled Multicentre Trial," *Lancet.* 359:1187-1193 (2002)); and Crohn's Disease (Sandborn et al., "Antitumor Necrosis Factor Therapy for Inflammatory Bowel Disease: A Review of Agents, Pharmacology, Clinical Results, and Safety," *Inflamm. Bowel Dis.* 5:119-133 (1999)).

Following adherence, the immune response of neutrophils involves chemotaxis, phagocytosis, and degranulation. Neutrophils sense and respond to gradients of activating agents (chemokines), which stimulate the neutrophil to move towards the gradient in a process known as chemotaxis (Brown S S., "Structure and Function of Profilin," *Cell Motil Cytoskel* 17:71-75 (1990); Southwick et al., "Contractile Proteins in Leukocyte Function," *Semin Hematol* 30:305-310 (1984)). Activated neutrophils are also capable of phagocytosing, i.e., engulfing foreign or damaged material, an important aspect of the inflammatory response. To engulf a particle, neutrophils extend pseudopodia, which engulf the offending material, trapping the material inside the cell in a compartment known is a phagosome (Wright S. D., "Receptors for Complement and the Biology of Phagocytosis," In *Inflammation* 2nd ed. 477-496 Raven Press New York (1992)). Cytoplasmic-bound granules, the primary and secondary granules of the neutrophil, which contain a multitude of effectors proteins, fuse with the phagosome, placing effector proteins in direct contact with the ingested material. Components of the primary granules include lysozyme, which can digest the peptidoglycan component of most bacterial cell walls, and elastase, cathepsin G, defensins, bacterial permeability-increasing protein (BPI), and myeloperoxidase, which converts hydrogen peroxide generated by NADPH oxidase and hydrochloric acid to hypochlorous acid, all with inherent antibacterial activity. Among the proteins contained in the secondary granules are lactoferrin, an iron-binding protein with some antibacterial activity. The secondary granules also contain stored sources of CR3 and other receptors for neutrophil activation agents, as well as stored membrane components of NADPH oxidase. NADPH oxidase is a crucial component of the neutrophil host defense mechanism. This enzyme assembles on the phagosomal membrane to generate superoxide anion from molecular oxygen and free electrons. Superoxide is then converted to the toxic metabolite hydrogen peroxide by the actions of superoxide dismutase, or to hypochlorous acid by the primary granule component myeloperoxidase (DeLeo et al., "Assembly of Phagocyte NADPH Oxidase: Molecular Interaction of Oxidase Proteins," *J. Leukocyte Biol* 60:677-691 (1996); Leusen et al., "Interactions Between the Components of the Human NADPH Oxidases: Intrigues in the Phox Family," *J. Clin Lab Med* 128: 461-476 (1996); Wientjes et al., NADPH Oxidase and the Respiratory Burst," *Semin Cell Biol* 6:357-365 (1995); Henderson et al., "NADPH Oxidases of Neutrophils," *Biochim Biophys Acta* 1273:87-107 (1996)). This ability to generate toxic oxygen metabolites is crucial to host defense against microbes.

The histotoxic impact of neutrophils is prominent in several inflammatory settings that are not thought to involve bacterial infection, such as rheumatoid arthritis, Crohn's Disease, and ischemia-perfusion syndrome, or in which neutrophil-mediated injury can occur at sites remote from invading bacteria, as in the acute respiratory distress and systemic inflammatory response syndromes. The stimuli that activate neutrophils in these settings are host-derived mediators (e.g., TNF), rather than bacteria themselves. What is needed is a method for inhibiting some inflammatory functions of activated neutrophils while sparing antimicrobial functions. Such a method would be particularly useful for preventing and treating inflammatory disorders related to respiratory burst in neutrophils mediated by effector proteins such as TNF.

The present invention is directed to overcoming these and other deficiencies in the art.

SUMMARY OF THE INVENTION

The present invention relates to a method of treating an inflammatory disorder in a subject. This method involves administering to a subject an effective amount of a compound selected from the group including the compound having the formula:

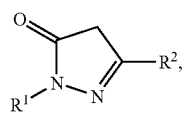

where $R^1$ is selected from the group consisting of: H, substituted or unsubstituted phenyl, and substituted or unsubstituted naphthalene, and where $R^2$ is selected from the group consisting of: H, $C_1$-$C_4$ alkyl, substituted or unsubstituted phenyl, $NH_2$, $CH_2COOCH_2CH_3$, and $COOCH_2CH_3$. Another compound for use in this method is a compound having the formula:

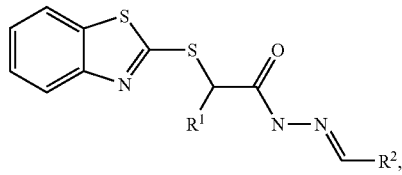

where $R^1$ is selected from the group consisting of: H and $C_1$-$C_4$ alkyl, and where $R^2$ is selected from the group consisting of: $C_1$-$C_4$ alkyl, substituted or unsubstituted phenyl, substituted or unsubstituted furan, substituted or unsubstituted cyclohexyl, substituted or unsubstituted naphthalene, substituted or unsubstituted indol, substituted or unsubstituted pyridine, and substituted or unsubstituted thiophene. Another compound for use in this method is a compound having the formula:

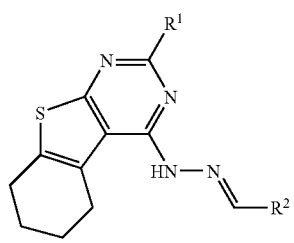

where $R^1$ is selected from the group consisting of: H and $C_1$-$C_4$ alkyl, and where $R^2$ is selected from the group consisting of: substituted or unsubstituted pyridine and substituted or unsubstituted phenyl. Yet another compound for use in this method is a compound having the formula:

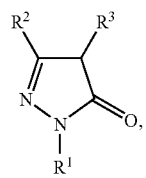

where $R^1$ is substituted or unsubstituted phenyl, $R^2$ is $C_1$-$C_4$ alkyl, and $R^3$ is a substituted or unsubstituted quinoline, with or without a linking group. Still another compound for use in this method of the present invention is a compound having the formula:

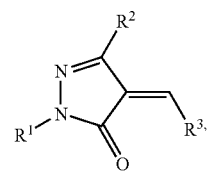

where $R^1$ is substituted or unsubstituted phenyl, $R^2$ is $C_1$-$C_4$ alkyl, and $R^3$ is substituted or unsubstituted benzoylhydrazino. These compounds are administered under conditions effective to treat the inflammatory disorder in the subject.

The present invention also relates to a method of inhibiting respiratory burst in adherent neutrophils without inhibiting neutrophil degranulation in or bacterial killing by neutrophils. This method involves contacting adherent neutrophils with an effective amount a chemical compound selected from the group including a compound having the formula:

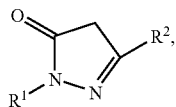

where $R^1$ is selected from the group consisting of: H, substituted or unsubstituted phenyl, and substituted or unsubstituted naphthalene, and where $R^2$ is selected from the group consisting of: H, $C_1$-$C_4$ alkyl, substituted or unsubstituted phenyl, $NH_2$, $CH_2COOCH_2CH_3$, and $COOCH_2CH_3$. Another compound for use in this method is a compound having the formula:

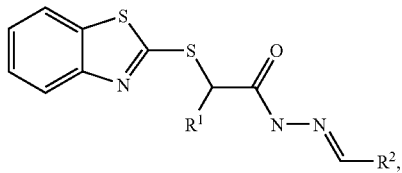

where $R^1$ is selected from the group consisting of: H and $C_1$-$C_4$ alkyl, and where $R^2$ is selected from the group consisting of: $C_1$-$C_4$ alkyl, substituted or unsubstituted phenyl, substituted or unsubstituted furan, substituted or unsubstituted cyclohexyl, substituted or unsubstituted naphthalene, substituted or unsubstituted indol, substituted or unsubstituted pyridine, and substituted or unsubstituted thiophene. Another compound for use in this method is a compound having the formula:

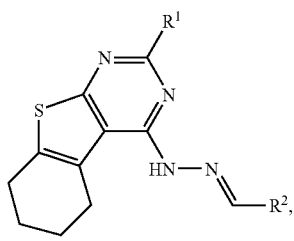

where $R^1$ is selected from the group consisting of: H and $C_1$-$C_4$ alkyl, and where $R^2$ is selected from the group consisting of: substituted or unsubstituted pyridine, and substituted or unsubstituted phenyl. Yet another compound for use in this method is a compound having the formula:

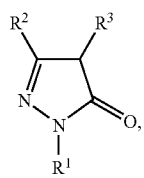

where $R^1$ is substituted or unsubstituted phenyl, $R^2$ is $C_1$-$C_4$ alkyl, and $R^3$ is selected from the group consisting of substituted or unsubstituted quinoline, with or without a linking group. Still another compound for use in this method of the present invention is a compound having the formula:

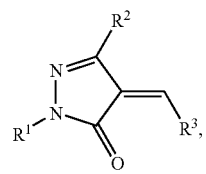

where $R^1$ is substituted or unsubstituted phenyl, $R^2$ is $C_1$-$C_4$ alkyl, and $R^3$ is substituted or unsubstituted benzoylhydrazino. These compounds are administered under conditions effective to inhibit respiratory burst in neutrophils without inhibiting deregulation in or bacterial killing by neutrophils.

Although neutrophil activation is crucial to both immunity and inflammation, it is clear that not all disorders warrant the full panoply of responses encompassed by neutrophil activation. The present invention provides a method of selectively inhibiting the immune and inflammatory responses triggered in neutrophils by cellular mediators, thereby preventing or treating an inflammatory disorder in a subject without compromising the subject's ability to stage an immune response against foreign microbes.

BRIEF DESCRIPTION OF THE DRAWINGS

FIG. 5A shows the effect of Comp I (23G01) on neutrophil regulatory burst; FIG. 5B shows the effect of Comp II (53F03); FIG. 5C shows the effect of Comp II' (9G01); FIG. 5D shows the effect of Comp III (55D01); FIG. 5E shows the effect of Comp IV (109G01), and FIG. 5F shows the effect of control Comp V (49G04).

FIGS. 6A-D show the effect of compounds 11C09, 11D09, 11G02, and 12D02, respectively, on TNF and PMA respiratory burst.

FIGS. 7A-C show, respectively, the effect of compounds 10E02, 10G04, and 11B09.

FIG. 9A shows respiratory burst of neutrophils incubated with DMSO (D), Comp II (53F03), Comp V (49G04)(V), or a buffer control (NS) for 30 min and stimulated with fMLF(100 nM). FIG. 9B shows respiratory burst of neutrophils incubated with DMSO (D), Comp I (23G01)(I), Comp III (55D01)(III), Comp IV (109G01)(IV), and Comp V (49G04)(V), or buffer control (NS) for 30 min and stimulated with fMLF(100 nM). $H_2O_2$ release is expressed as means±SEM for triplicates.

FIG. 10A shows the results using Comp II as active molecule and Comp V as inactive molecule. FIG. 10B shows inhibition by Comp I, III, and IV, compared to Comp V and DMSO controls. $H_2O_2$ release is expressed as means±SEM for triplicates.

FIG. 12A shows results with Comp II (53F03) and Comp V (49G04). FIG. 12B shows results with Comp I, III, IV, and V.

FIGS. 14A-D show the impact of Comp I-V on several known tyrosine kinases. FIG. 14A shows the effect of Comp I-V on TNF triggered tyrosine phosphorylation of total cellular proteins. Neutrophil lysates, prepared as indicated in the examples, were separated by SDS-PAGE and western-blotted (WB) with anti-phosphotyrosine antibody. FIG. 14B shows the effect of Comp I-IV on TNF triggered Src activity. Recombinant Src kinase was incubated with each compound and assayed for its kinase activity in vitro. FIG. 14C shows the effect of Comp I-V on TNF triggered Syk activity. Syk was immunoprecipitated from neutrophils treated as indicated and probed with anti-phosphotyrosine antibody (PY) (upper row) or anti-Syk antibody (lower row). FIG. 14D shows the activity of recombinant Syk pre-incubated with Comp I, II, III, IV or V, DMSO (D) or and measured in vitro.

DETAILED DESCRIPTION OF THE INVENTION

Figure 1:
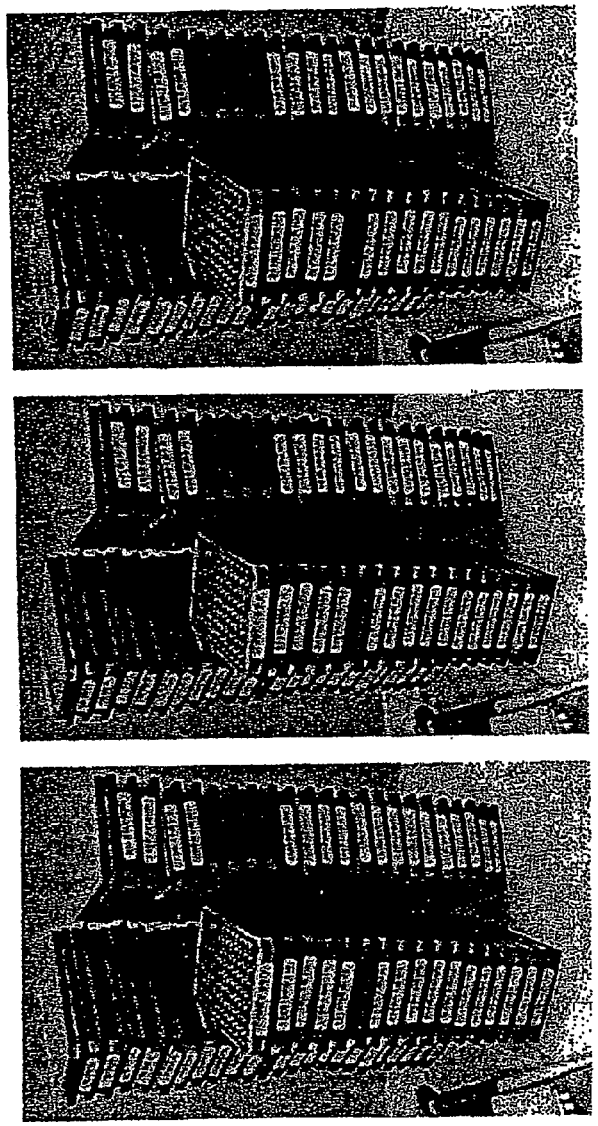
FIG. 1 shows the combinatorial chemistry scheme for screening 15,000 compounds for inhibition of neutrophil respiratory burst.

The present invention relates to a method of treating an inflammatory disorder in a subject. This method involves administering to a subject an effective amount of a compound under conditions to treat the inflammatory disorder. One suitable compound for use in carrying out this method is a compound having the general formula:

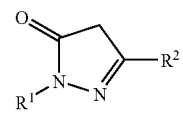

where $R^1$ is H, substituted or unsubstituted phenyl, or substituted or unsubstituted naphthalene, and $R^2$ is H, $C_1$-$C_4$ alkyl, substituted or unsubstituted phenyl, $NH_2$, $CH_2COOCH_2CH_3$, or $COOCH_2CH_3$. One embodiment of this compound, called hereinafter 53F03 (also called Comp I herein), has the formula:

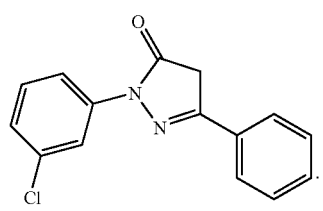

53F03

2-(3-Chloro-phenyl)-5-phenyl-2,4-dihydro-pyrazol-3-one

Another suitable compound for use in this method has the general formula:

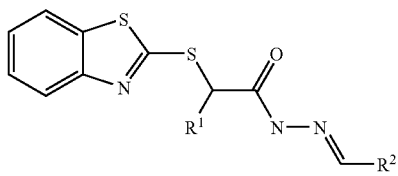

where $R^1$ is H or $C_1$-$C_4$ alkyl, and $R^2$ is $C_1$-$C_4$ alkyl, substituted or unsubstituted phenyl, substituted or unsubstituted furan, substituted or unsubstituted cyclohexyl, substituted or unsubstituted naphthalene, substituted or unsubstituted indol, substituted or unsubstituted pyridine, or substituted or unsubstituted thiophene. One embodiment of this compound, called hereinafter 109G01, has the formula:

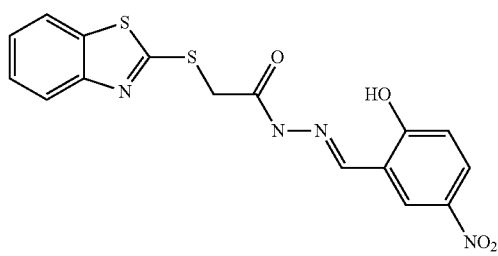

109G01

(Benzothiazol-2-ylsulfanyl)-acetic acid (2-hydroxy-5-nitro-benzylidene)-hydrazide Yet another suitable compound for use in this method of the present invention has the general formula:

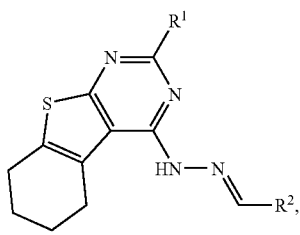

where $R^1$ is H or $C_1$-$C_4$ alkyl, and $R^2$ is substituted or unsubstituted pyridine or substituted or unsubstituted phenyl. One embodiment this compound, called 55D01 hereinafter, has the formula:

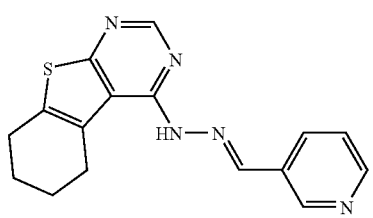

55D01

N-Pyridin-3-ylmethylene-N-(5,6,7,8-tetrahydro-benzo[4,5][2,3-a]pyrimidin-4-yl)-hydrazine Another embodiment of this compound, called 23G01 hereinafter, has the formula:

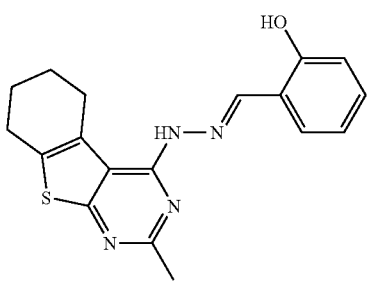

23G01

2-[(2-Methyl-5,6,7,8-tetrahydro-benzo[4,5]thieno[2,3-a]pyrimidin-4-yl)-hydrazonomethyl]-phenol Yet another suitable compound for use in this aspect of the present invention is a compound having the general formula:

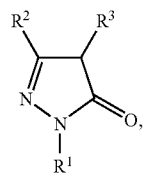

where $R^1$ is substituted or unsubstituted phenyl; $R^2$ is $C_1$-$C_4$ alkyl, and $R^3$ is substituted or unsubstituted quinoline, with or without a linking group. A preferred embodiment of this general compound is the compound called hereinafter 9G01 (also called Comp II'), having the formula:

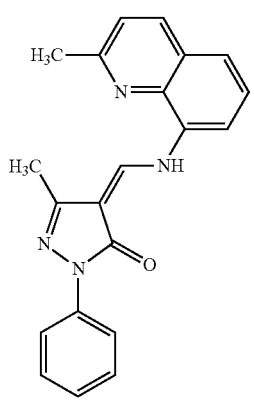

9G01

Still another suitable compound for use in this method of the present invention is a compound having the general formula:

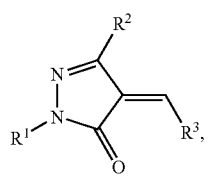

where R[1] is substituted or unsubstituted phenyl; R[2] is $C_1$-$C_4$ alkyl, and R[3] is substituted or unsubstituted benzoylhydrazino. Exemplary compounds having this general formula as a base include, without limitation, the compound called hereinafter 10E02, having the formula:

10E02

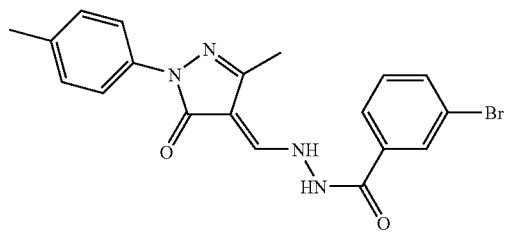

3-Bromo-benzoic acid N'-(3-methyl-5-oxo-1-p-tolyl-1,5-dihydro-pyrazol-4-ylidenemethyl)-hydrazide A second suitable compound of this aspect of the present invention having the same generic base formula as 10E02 is the compound called 10G04 hereinafter, having the following formula:

10G04

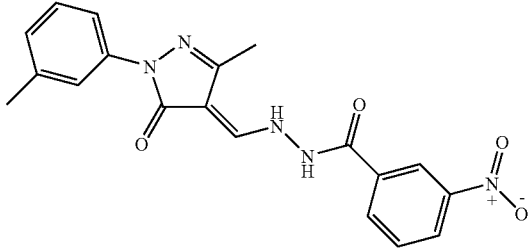

3-Nitro-benzoic acid N'-(3-methyl-5-oxo-1-m-tolyl-1,5-dihydro-pyrazol-4-ylidenemethyl)-hydrazide Also included in this group, without limitation, are the following compounds: 11B09, having the formula:

11B09

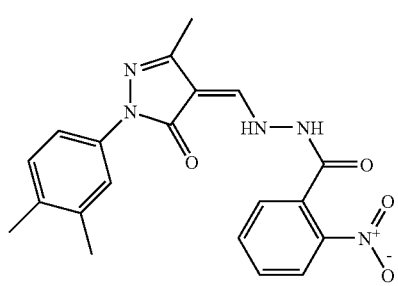

2-Nitro-benzoic acid N'-[1-(3,4-dimethyl-phenyl)-3-methyl-5-oxo-1,5-dihydro-pyrazol-4-ylidenemethyl]-hydrazide;

11C09, having the formula:

11C09

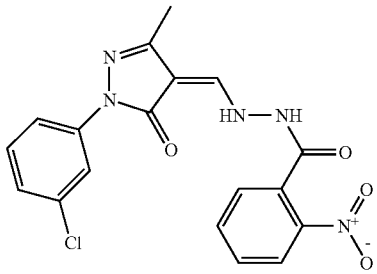

2-Nitro-benzoic acid N-[1-(3-chloro-phenyl)-3-methyl-5-oxo-1,5-dihydro-pyrazol-4-ylidenemethyl]-hydrazide;

11D09, having the formula:

11D09

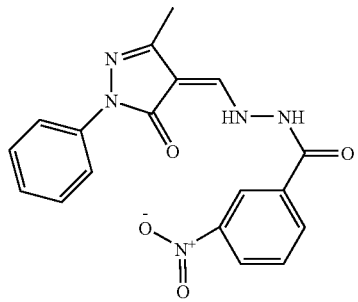

3-Nitro-benzoic acid N'-(3-methyl-5-oxo-1-phenyl-1,5-dihydro-pyrazol-4-ylidenemethyl)-hydrazide;

11G02, having the formula:

11G02

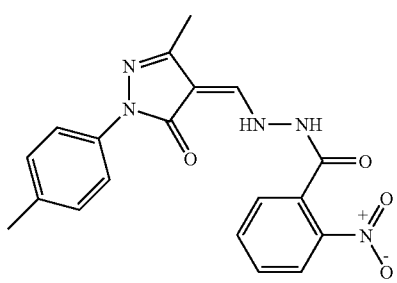

2-Nitro-benzoic acid N'-3-methyl-5-oxo-1-tolyl-1,5-dihydro-pyrazol-4-ylidenemethyl)-hydrazide;

and 12D02, having the formula:

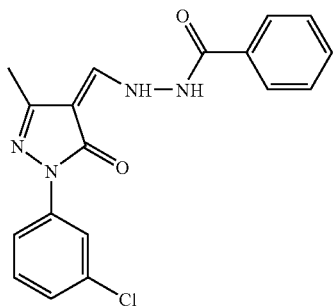

12D02

Benzoic acid N'-[3-chloro-phenyl)-3-methyl-5-oxo-1,5-dihydro-pyrazol-4-ylidenemethyl]-hydrazide The above compounds are available from Chemical Diversity, Inc., (San Diego, Calif.).

In all embodiments of this method of the present invention, the compounds are administered to a subject under conditions effective to treat the inflammatory disorder.

The compounds used according to the methods of the present invention can be administered alone or as a pharmaceutical composition, which includes the compound(s) and a pharmaceutically-acceptable carrier. The compounds of the present invention are typically provided as a pharmaceutical composition. The pharmaceutical composition can also include suitable excipients, or stabilizers, and can be in solid or liquid form such as tablets, capsules, powders, solutions, suspensions, or emulsions. Typically, the composition will contain from about 0.01 to 99 percent, preferably from about 5 to 95 percent of active compound(s), together with the carrier.

The compounds of the present invention, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, for example, that of the nose, throat, and bronchial tubes including, for example, by inhalation.

For most therapeutic purposes, the compounds can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, the compound in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

For transdermal routes, the compound is present in a carrier which forms a composition in the form of a cream, lotion, solution, and/or emulsion. The composition can be included in a transdermal patch of the matrix or reservoir type as are conventional in the art for this purpose.

All mammals are suitable subjects for use in methods of the present invention, including, but not limited to, humans.

Suitable disorders to be treated or prevented in all aspects of the present invention present herein above or below are disorders in which a major pathogenic role is assigned to inflammation, including, without limitation, ischemia-reperfusion injury (occlusive and embolic stroke and myocardial infarction, type I diabetes mellitus, asthma, chronic obstructive pulmonary disease, gout, pre-term labor, sarcoidosis, ulcerative colitis, rheumatoid arthritis, osteoarthritis, xenograft rejection, Hashimoto's thyroiditis, ankylosing spondylitis, psoriasis, pemphigus, chronic obstructive pulmonary disease, systemic lupus erythematosus, atopic dermatitis, vasculitides (Wegener's Syndrome, Goodpasture's Syndrome, giant cell arteritis, polyarteritis nodosa), multiple sclerosis, Alzheimer's Disease, and Crohn's Disease (regional enteritis).

The method of the present invention is also useful for treating diseases of infectious origin in which inflammation may contribute as much to pathology as does microbial toxicity, including, without limitation, sepsis syndrome, post-streptococcal glomerulonephritis, hepatitis C, *Neisserial* or *Pneumococcal* meningitis, *Helicobacter pylori* gastritis, influenza virus pneumonia, tuberculosis, leprosy (tuberculoid form), filariasis, cystic fibrosis, bacterial dysentery, and Chagas Disease (*Trypanosoma cruzi*).

Additional conditions or disorders encompassed by the methods of the present invention are diseases of diverse origin in which post-inflammatory fibrosis is a major cause of pathology. These diseases include, without limitation: schistosomiasis, idiopathic pulmonary fibrosis, hepatic cirrhosis (post-viral or alcoholic), radiation-induced pulmonary fibrosis, chronic allograft rejection, and bleomycin-induced pulmonary fibrosis.

Another aspect of the present invention is a method of inhibiting respiratory burst in adherent neutrophils without inhibiting neutrophil degranulation in or bacterial killing by the neutrophils. This method involves contacting adherent neutrophils with an effective amount of the above listed chemical compounds. This involves the formulations and modes of administration described above.

This aspect of the present invention may be carried out by contacting adherent neutrophils in vitro using methods known in the art, including, but not limited to, adding the compounds described herein above to adherent neutrophils in a suitable cell culture system. This aspect of the present invention may also be carried out by contacting neutrophils in vivo as described above.

In this method of the present invention, where contacting with a compound of the present invention inhibits respiratory burst in adherent neutrophils, the respiratory burst is triggered by an protein effector agent such as a chemokine, a cytokine, a complement component, a bacterium, or a bacterial factor.

Suitable chemokines for this aspect of the present invention include, without limitation, macrophage inflammatory protein-1 (MIP-1) and interleukin-8 (IL-8), as well as the chemoattractant complement component C5a.

Suitable cytokines for this aspect of the present invention include, without limitation, tumor necrosis factor (TNF), lymphotoxin, granulocyte-specific colony stimulating factor (G-CSF), and granulocyte/macrophage-specific colony stimulating factor (GM-CSF).

Also suitable as a trigger of respiratory burst in this aspect of the present invention are bacteria. This includes, without limitation, whole bacteria, bacterial cell wall components, and secreted or shed bacterial products.

Suitable bacteria of this aspect of the present invention include, without limitation, the Gram-negative bacterium *Salmonella enterica* Var. *typhimurium* and the Gram-positive bacterium *Listeria monocytogenes*. Suitable secreted or shed bacterial products of this aspect of the present invention include, without limitation, amino-terminally formylated peptides such as N-formyl-methionyl-leucyl-phenylalanine (fMLF).

EXAMPLES

Example 1

Screening of Chemical Library for Specific Inhibitors of TNF and PMA-Triggered $H_2O_2$ Release Chemical Library High Throughput Screening (HTS) of a chemical compound library selected by Dr. Tarun Kapoor at Rockefeller University was carried out to identify specific inhibitors of TNF and PMA-triggered $H_2O_2$ release by primary human neutrophils. As shown in FIG. 1, the library used for screening consists of 15,000 compounds generated from 125 combinatorial templates each template with 200 different side chain modifications. The compounds are "drug like" compounds, i.e., small molecules that have high membrane permeability for efficient delivery of molecules across the cell membrane. Out of the 15,000 compounds screened, 460 compounds showed over 90% inhibition at 20 μM during primary screening. Among the 460, 190 were tested against both TNF and PMA triggered $H_2O_2$ release to eliminate toxic compounds for neutrophils and inhibitors of protein kinase C (PKC) or the assay itself. After several conformational tests (to eliminate donor-donor variation), a small number of compounds, identified herein above, were identified as capable of inhibiting TNF triggered respiratory burst, as measured by $H_2O_2$ release, without inhibiting PMA-triggered respiratory burst. These compounds were used for additional studies.

Neutrophil Isolation

Neutrophils were isolated to >95% purity from heparinized (10 U/ml) blood of normal human donors using Polymorphprep™ (Axis-Shield PoC AS, Norway) according to the manufacturer's instructions. Contaminating erythrocytes were lysed by hypotonic shock for 45 seconds with 0.2% saline. Neutrophils were resuspended in Krebs-Ringer phosphate with glucose (KRPG) formulated as described (De la Harpe et al., "A Semi-Automated Micro-Assay for H2O2 Release by Human Blood Monocytes and Mouse Peritoneal Macrophages," *J Immunol Methods* 78:323-336 (1985), which is hereby incorporated by reference in its entirety).

Automated Assay Screening

Figure 2:
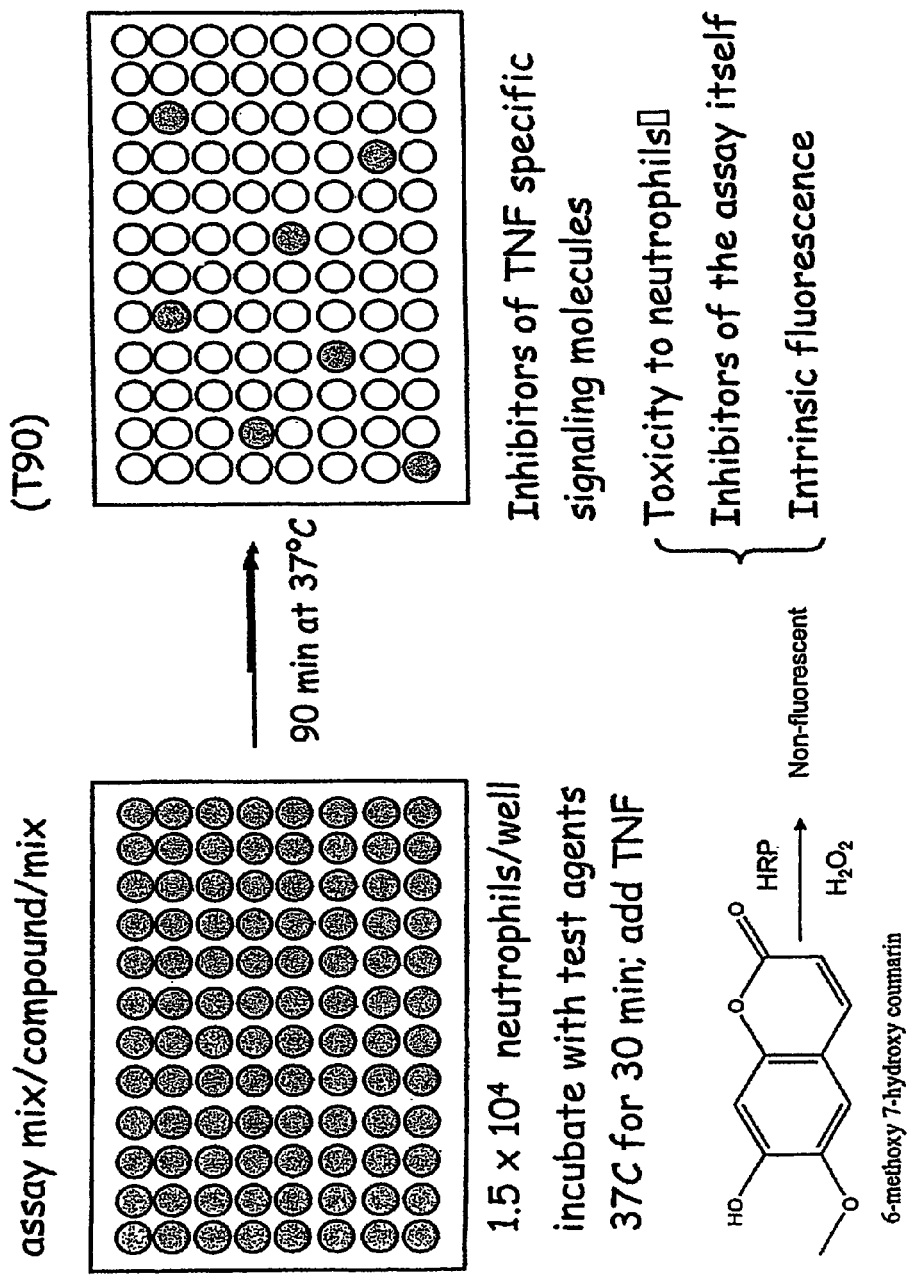
FIG. 2 is a diagram showing the TNF-inhibition assay used for initial screening of compounds from the combinatorial library.
Figure 3:
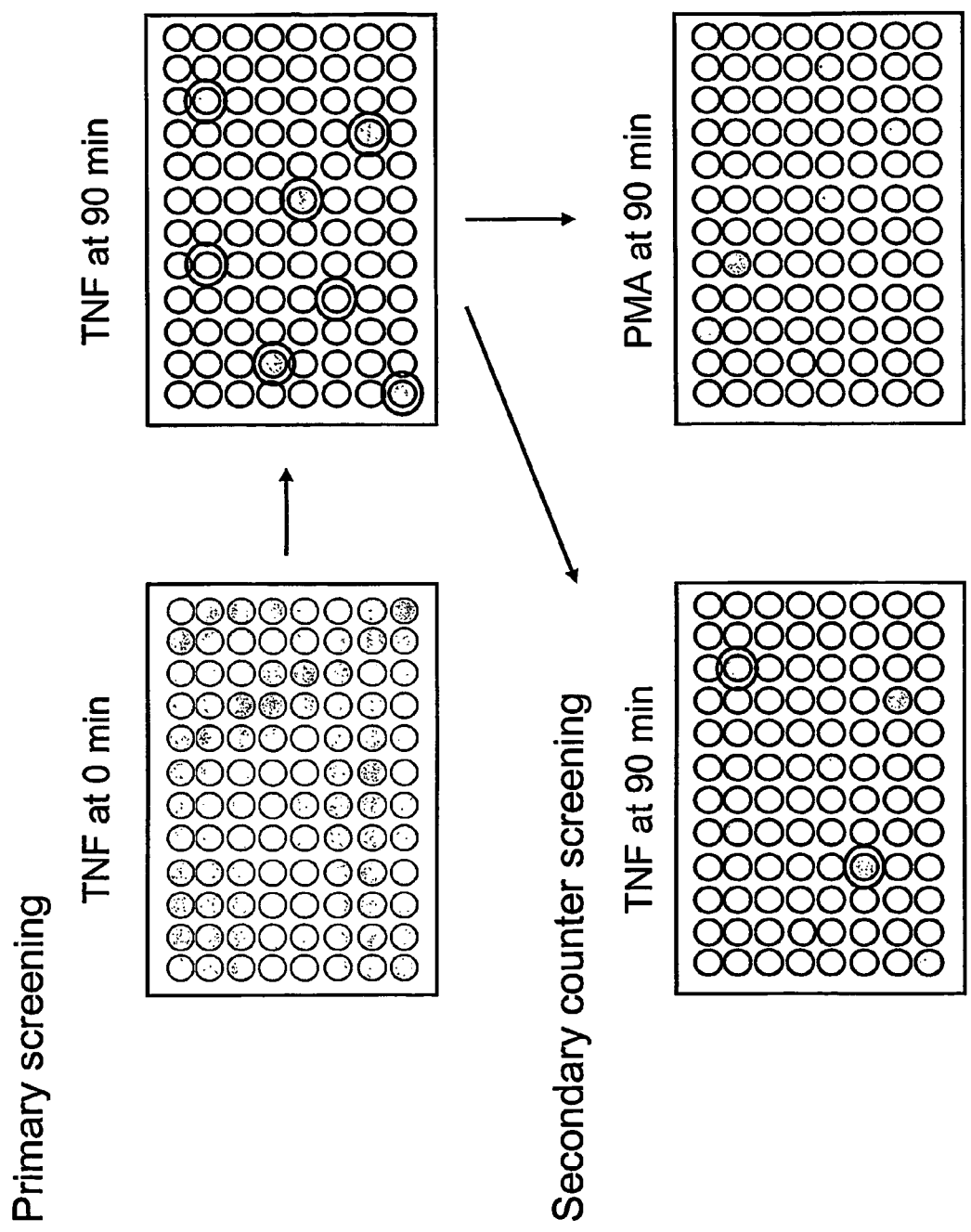
FIG. 3 is a diagram of TNF-PMA counter-screening of potentially useful compounds from the combinatorial library.

FIGS. 2-3 demonstrate the screening scheme that identified the compounds of the present invention. Briefly, 15,000 compounds were screened to identify specific inhibitors of TNF-triggered $H_2O_2$ release in human neutrophils. $H_2O_2$ release was measured as above except a few modifications to adapt to high throughput screening. Black, instead of clear, 96-well tissue culture plates (Falcon, Cat. No. 353945, Fisher Scientific, Hampton, NH) were used to reduce the background fluorescence reading. Perkin-Elmer Fusion microplate reader was used for recording fluorescence, Titertek Multidrop 96/384 for bulk reagent dispensing, Bi-Tek Elx 405 Select Plate Wash system for plate washing, and Perkin Elmer MiniTrakV liquid handling robot (Perkin Elmer, Foster City, Calif.) for the delivery of compound aliquots to each well. Percent inhibition by each compound was calculated using the formula:

$$\frac{(T0 - T90) \times 100}{(Tc0 - Tc90)}$$

Figure 4:
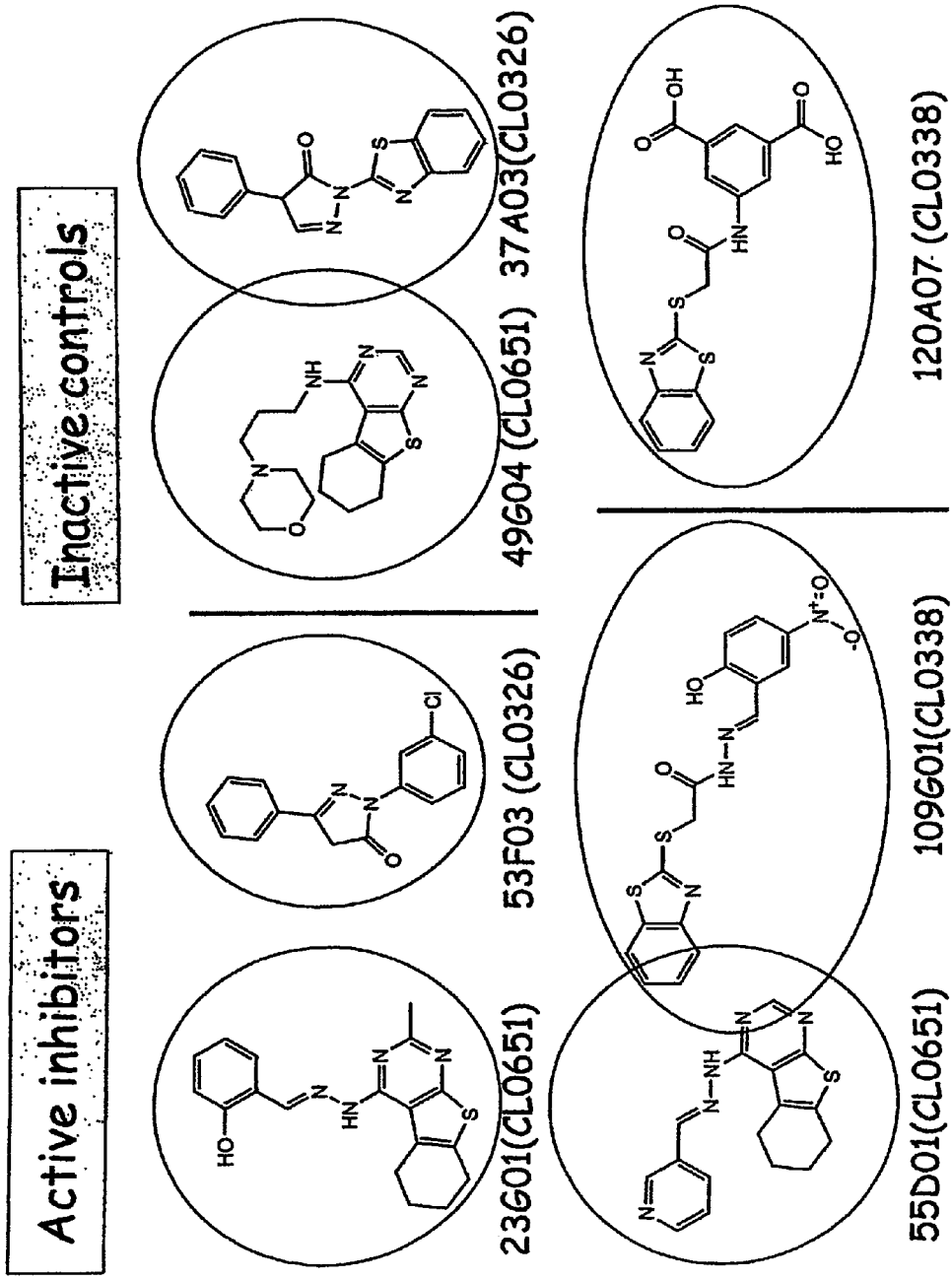
FIG. 4 shows some of the compounds found to be active or inactive during the screening process.
Figure 5:
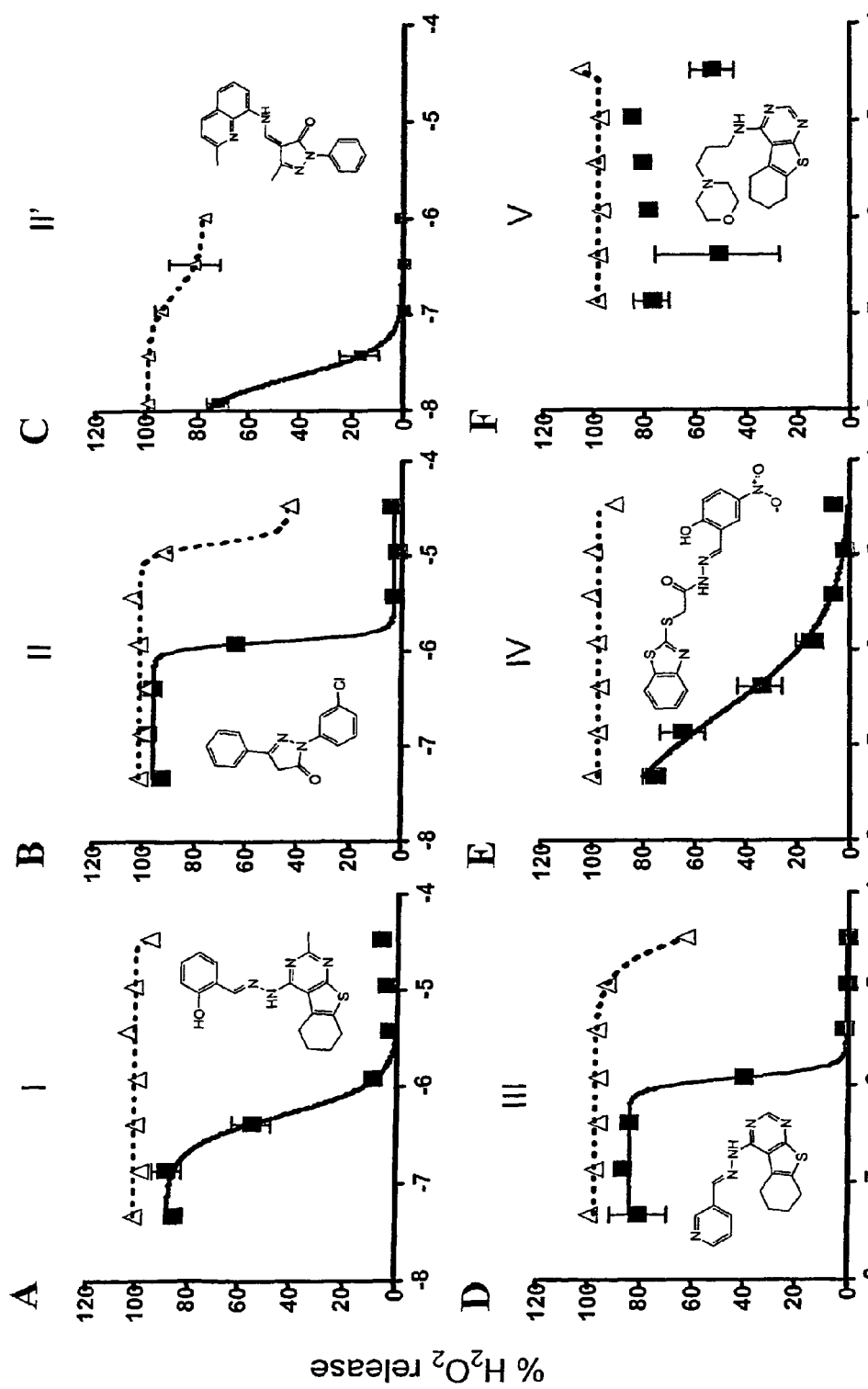
FIGS. 5A-F show several small chemical compounds that separately control neutrophil respiratory burst and degranulation. Neutrophils were incubated with the indicated concentrations of each compound for 37° C. for 30 min before stimulation with TNF (100 ng/ml, σ). $H_2O_2$ release measured at 90 min is displayed as % $H_2O_2$ release of TNF or PMA alone, in the absence of any compound.
Figure 6:
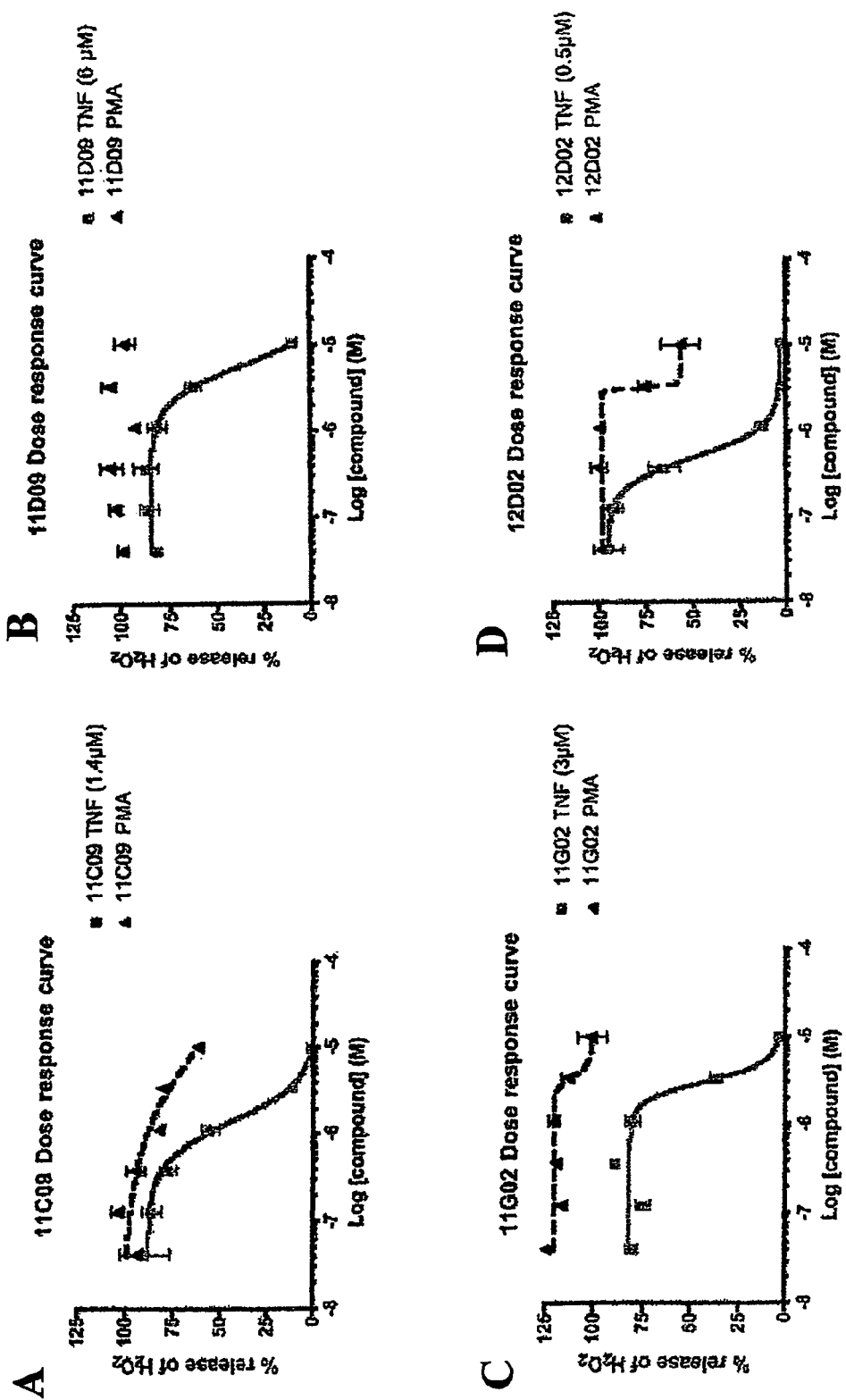
FIGS. 6A-D show the effect of other small compounds of the present invention on TNF and PMA triggered neutrophil respiratory burst and degranulation. The experiments were carried out essentially as described for FIGS. 5A-F.

T0 and T90 are fluorescence readings at each well at 0 and 90 min, respectively. Tc0 and Tc90 are the mean fluorescence readings in the compound free control wells at 0 and 90 min, respectively. Compounds that showed over 90% inhibition on TNF triggered respiratory burst were retested on both TNF and PMA triggered burst to eliminate non-specific, toxic chemicals or PKC inhibitors. Some of the compounds found to be active or inactive using the screening schema shown in FIGS. 1-3 are shown in FIG. 4.

Morphology

Glass coverslips were placed in 12 well tissue culture plate and coated with FBS in 5% $CO_2$ at 37° C. for at least 1 h and washed three times with 0.9% saline. Neutrophils ($2 \times 10^6$) were added to each well containing a FBS-coated glass coverslip and 1 ml of reaction mixture and incubated or not with each compound at 37° C. for 30 min before stimulation with TNF (100 ng/ml), PMA (100 ng/ml) or an equal volume of KRPG. Cells were fixed with 2% paraformaldehyde and 3.7% formaldehyde buffer, and photographed with phase-contrast microscope.

Example 2

$H_2O_2$ Release and Degranulation of Neutrophils

Respiratory burst was measured as described elsewhere (De la Harpe et al., "A Semi-Automated Micro-Assay for H2O2 Release by Human Blood Monocytes and Mouse Peritoneal Macrophages," *J Immunol Methods* 78:323-336 (1985), which is hereby incorporated by reference in its entirety). Briefly, 96-well flat-bottomed plates (Primaria, Falcon) were coated with 50 μl/well of FBS in 5% $CO_2$ at 37° C. for at least 1 h and washed three times with 0.9% saline. Neutrophils ($1.5 \times 10^4$) were added to triplicate wells containing 100 μl of reaction mixture (2.4 nm scopoletin, 0.5 μg horseradish peroxidase (HRP), and 1 mM $NaN_3$) and stimulated with either buffer control, TNF (PreproTech, London, UK) or phorbol myristate acetate (PMA), each at 100 ng/ml.

The reduction of scopoletin by $H_2O_2$ was recorded every 15 min on a plate-reading fluorometer until $H_2O_2$ release reached plateau and the amount of $H_2O_2$ released calculated as described (De la Harpe et al., "A Semi-Automated Micro-Assay for $H_2O_2$ Release by Human Blood Monocytes and Mouse Peritoneal Macrophages," *J Immunol Methods* 78:323-336 (1985), which is hereby incorporated by reference in its entirety). The supernatant from the $H_2O_2$ release assay with $1.5 \times 10^4$ neutrophils was used to measure degranulation using lactoferrin (LF) or myeloperoxidase (MPO) ELISA kit (Oxis International, Inc., Portland, Oreg.). Spontaneous cell death from the same supernatant was measured using Cytotoxicity Detection Kit (Roche Molecular Biochemicals, Nutley, N.J.). The total cell content of LF, MPO, and lactate dehydrogenase (LDH) was determined after lysing cells with 1% Triton X100. LDH is a cytosolic enzyme whose release indicates cell lysis, such that high release of LF or MPO in the face of low release of LDH is taken as a measure of degranulation. As shown in FIGS. 5A-F, and FIGS. 6A-D, $H_2O_2$ release measured at 90 min is displayed as % $H_2O_2$ release of TNF or PMA alone, in the absence of any compound.

Figure 7:
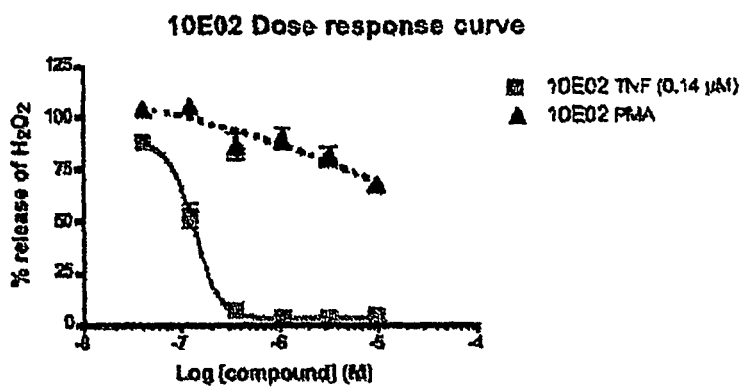
FIGS. 7A-C show the effect of still more small molecule compounds of the present invention on TNF and PMA triggered neutrophil respiratory burst and degranulation. The experiments were carried out essentially as described for FIGS. 5A-F.
Figure 7:
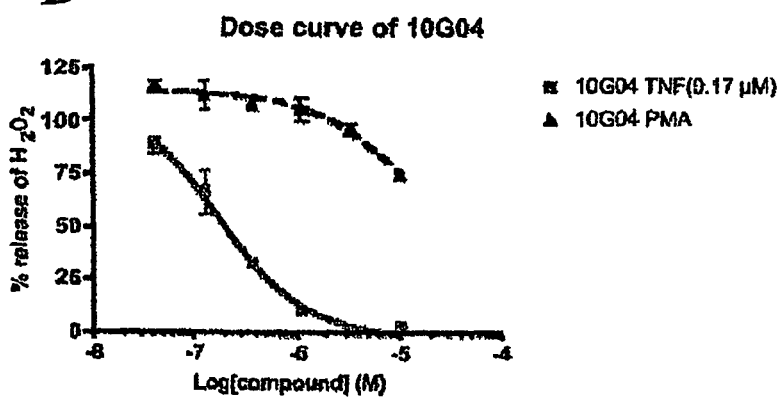
Figure 7:
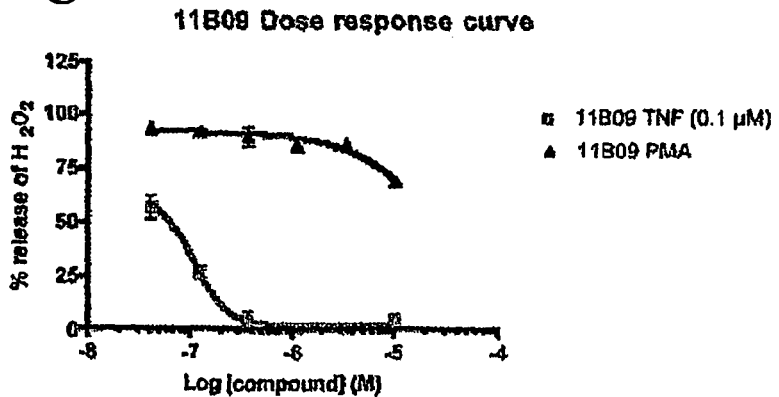

Four of the compounds of the present invention proved particularly interesting after several rounds of conformational testing, and these were used for most of the examples described herein. The chemical structures of the five specific compounds are illustrated in FIGS. 5A-F. The structures, referred to as Comp I, II, II', III, and IV in the Figures and Examples, correspond to compound 23G01, 53F03, 9G01, 55D01, 109G01, respectively, as described herein above. Comp V, also known as 49G04, shows no effect on $H_2O_2$ release, and was used as an inactive control in all the subsequent experiments. Dose response curves for these compounds are shown in FIGS. 5A-F. $IC_{50}$ of Comp I is about $0.18 \pm 0.04$ μM, $1.6 \pm 0.4$ μM for Comp II, 22 nm for Comp II', and $2.5 \pm 1.5$ μM for Comp III. Interestingly, Comp IV displayed very variable $IC_{50}$ ranging from 3 nM-2 μM. These discrepancies do not seem to be due to donor-to-donor variations or byproducts of compound breakdown. The nature of variation in $IC_{50}$ for Comp V is not currently understood. Understanding the nature of it might help in the development of a more potent antagonist of neutrophil activation. Concentration that consistently yielded over 95% inhibition on TNF triggered RB was empirically decided for each compound and used for all the subsequent experiments: 2 μM for Comp I, 5 μM for Comp II, III, and V, 1 μM for Comp II', and 10 μM for Comp IV. None of the compounds seems to be toxic for long term incubation tested by TNF and γ-IFN induced NO release by mouse macrophages. FIGS. 6A-D show the on TNF and PMA triggered $H_2O_2$ release using compounds 11C09, 11D09, 11G02, and 12D02, respectively, and FIGS. 7A-C show the effect of compounds 10E2, 10G04, and 11B09, respectively.

Example 3

Test of Reversibility of TNF Inhibitory Effect

Figure 8:
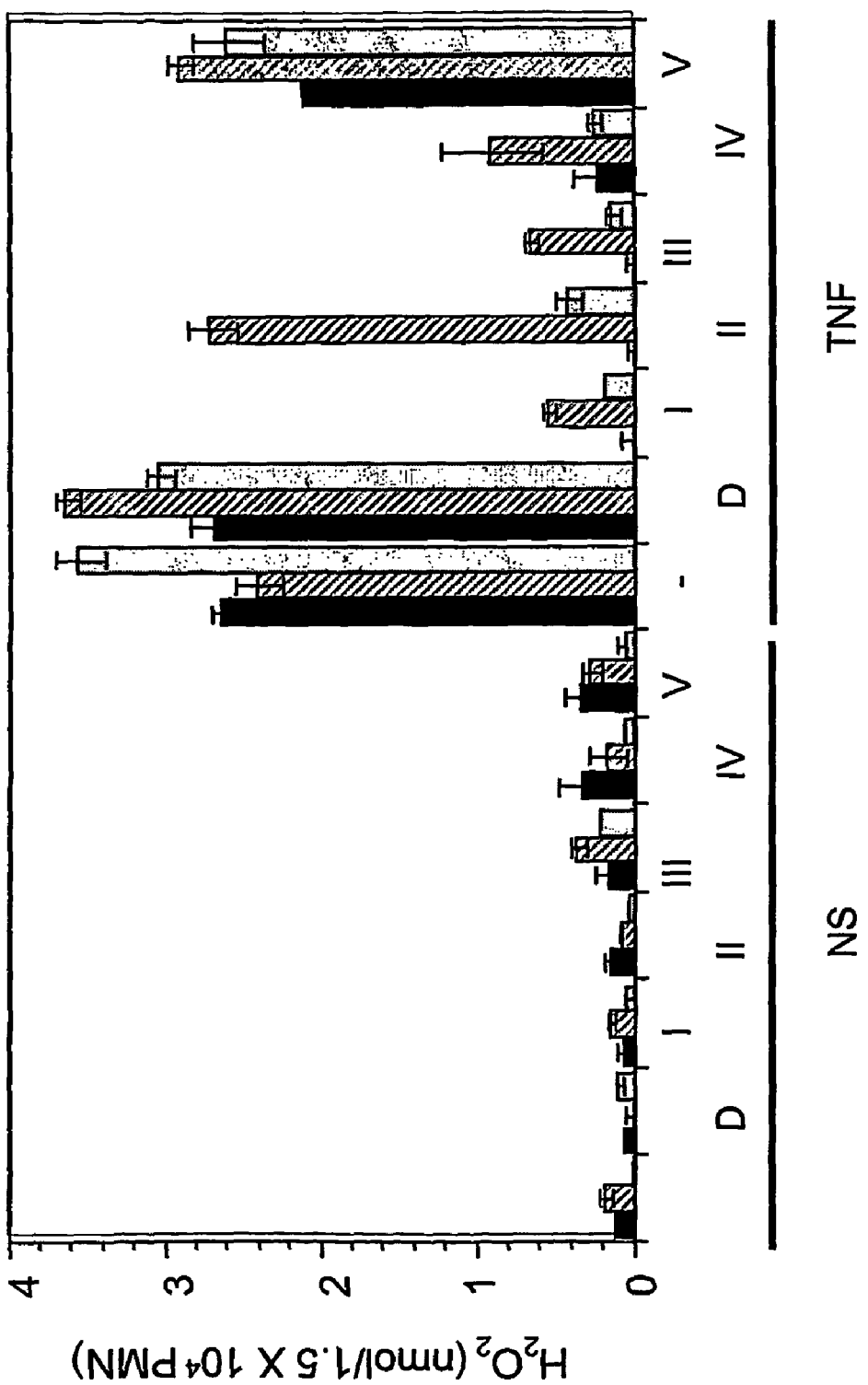
FIG. 8 shows the reversibility of the inhibition of TNF triggered respiratory burst by compounds of the present invention. Neutrophils incubated with DMSO (D) or each compound (I-V) were washed (hatched bar) or not (black solid bar) with cold KRPG and plated in 96 well plates before stimulation with TNF (100 ng/ml) or an equivalent volume of KRPG buffer as control. On a separate plate, compounds were added back to the neutrophils from which compounds had been washed off, and cells were stimulated to ensure neutrophils' capacity to respond. Results are expressed as means±SEM for triplicates.

Neutrophils were incubated with test compounds I-V or DMSO at 37° C. for 30 min in FBS coated tubes (Falcon, Cat. Number 352063), washed twice with cold KRPG, and plated in 96 well plates before stimulation with TNF (100 ng/ml) or an equivalent volume of KRPG buffer as a control. On a separate plate, compounds were added back to the neutrophils that were washed off compounds, and cells were stimulated to ensure neutrophils' capacity to respond. Neutrophils incubated with each compound without washing were also stimulated for comparison. FIG. 8 shows the results of the reversibility test. Comp II appears to have the greatest reversibility.

Example 4

Effect of Compound II on fMLF or Bacteria Triggered Respiratory Burst

Figure 9A:
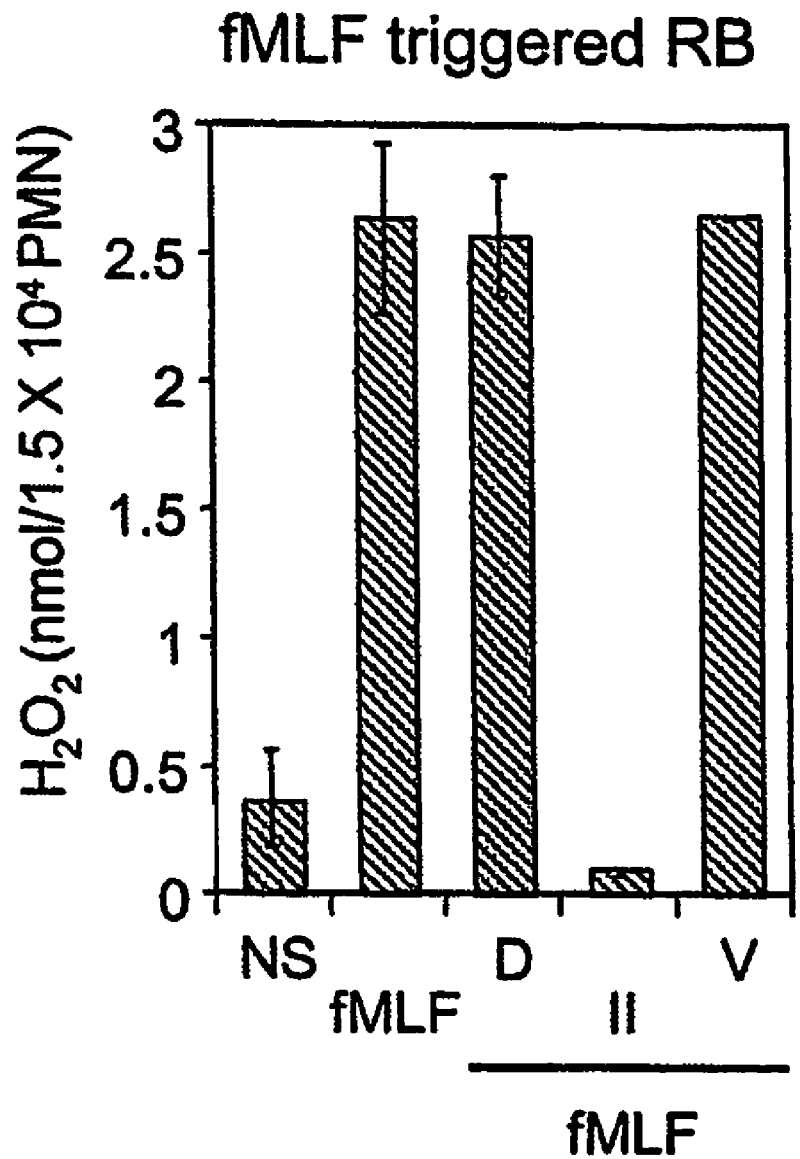
FIGS. 9A-B shows the effect of N-formyl-methionyl-leucyl-phenylalanine (fMLF) stimulated respiratory burst when neutrophils are treated with compounds of the present invention.
Figure 9:
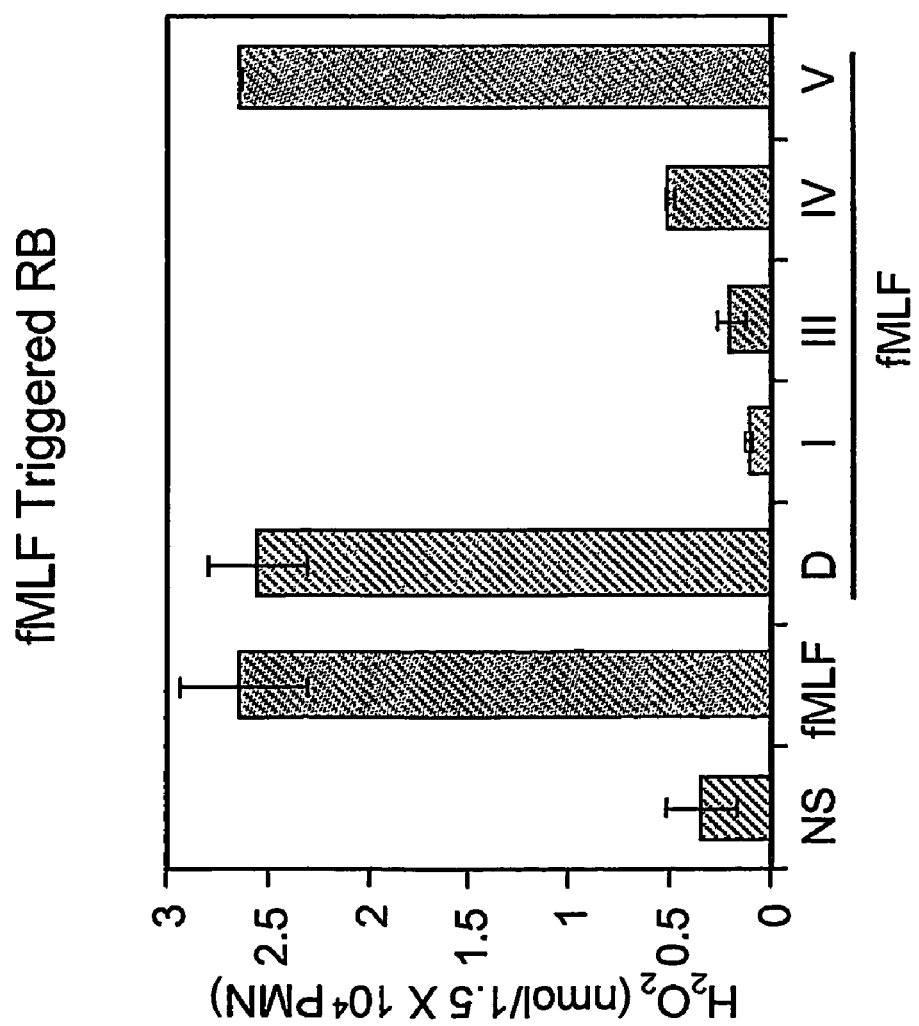
Figure 10A:
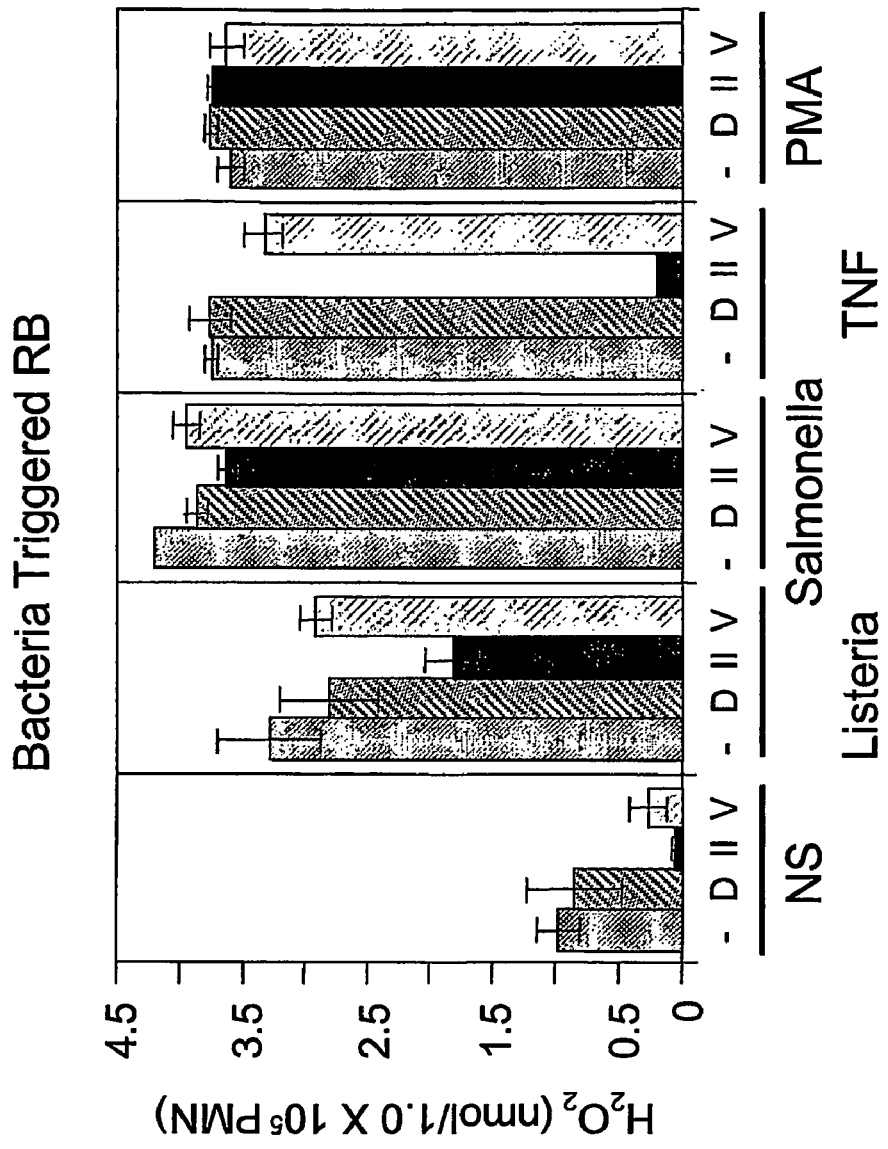
FIGS. 10A-B shows the results of bacteria triggered respiratory burst when neutrophils are treated with the small molecule compounds of the present invention prior to triggering respiratory burst by contact with bacteria. Neutrophils were incubated with either DMSO (D), Comp I-V, or a buffer control (NS) for 30 min and stimulated with *L. monocytogenes* or *S. typhimurium*.
Figure 10B:
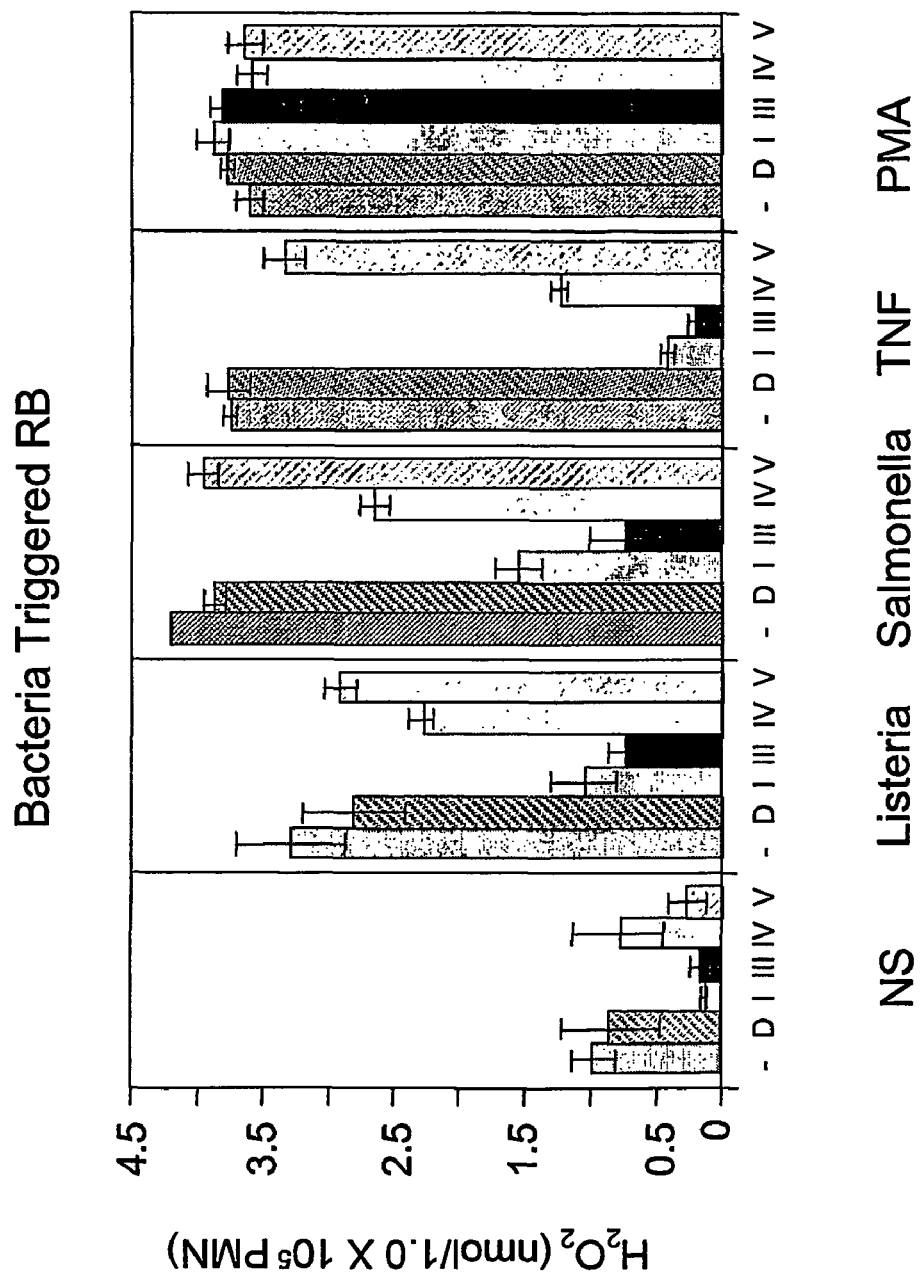

The effects of each compound on the interactions between neutrophil and bacteria or bacterial product were also assessed. Neutrophils isolated as described above were incubated with selected compound for 30 min and stimulated with FMLF (100 nM) or by contact with *L. monocytogenes* or *S. typhimurium*. For the bacteria triggered samples, neutrophils were incubated with DMSO or a compound for 30 min at 37° C. and then exposed to 10% autologous serum-opsonized *Salmonella typhimurium* (ATCC 14028s) (a Gram-negative bacterium) or *Listeria monocytogenes* (ATCC 104035) (a Gram-positive bacterium), at a multiplicity of infection of 0.5 bacteria per neutrophil. $H_2O_2$ release was measured as above. The results of the assay are represented by Comp II because it showed the greatest reversibility and consistency. FIG. 9A shows the effect of Comp II and Comp V on fMLF stimulated respiratory burst. FIG. 9B shows the effect of Comp I, III, IV, and V on on fMLF stimulated respiratory burst in human neutrophils. FIG. 10A shows the effect of Comp I and Comp V on bacteria-triggered respiratory burst. The effect of Comp II-V on bacteria-triggered respiratory burst in neutrophils is shown in FIG. 10B. $H_2O_2$ release triggered by fMLF, a bacteria-released chemoattractant, was blocked by all four active compounds. However, none of the four active compounds inhibited $H_2O_2$ release triggered by *Salmonella typhimurium* or *Listeria monocytogenes* and killing of these pathogens by neutrophils. Thus, it appears that these compounds target specific pathway(s) that are triggered by small soluble molecules such as cytokines and chemokines.

Example 5

Influence on the TNF Triggered Degranulation of Neutrophils

Figure 11:
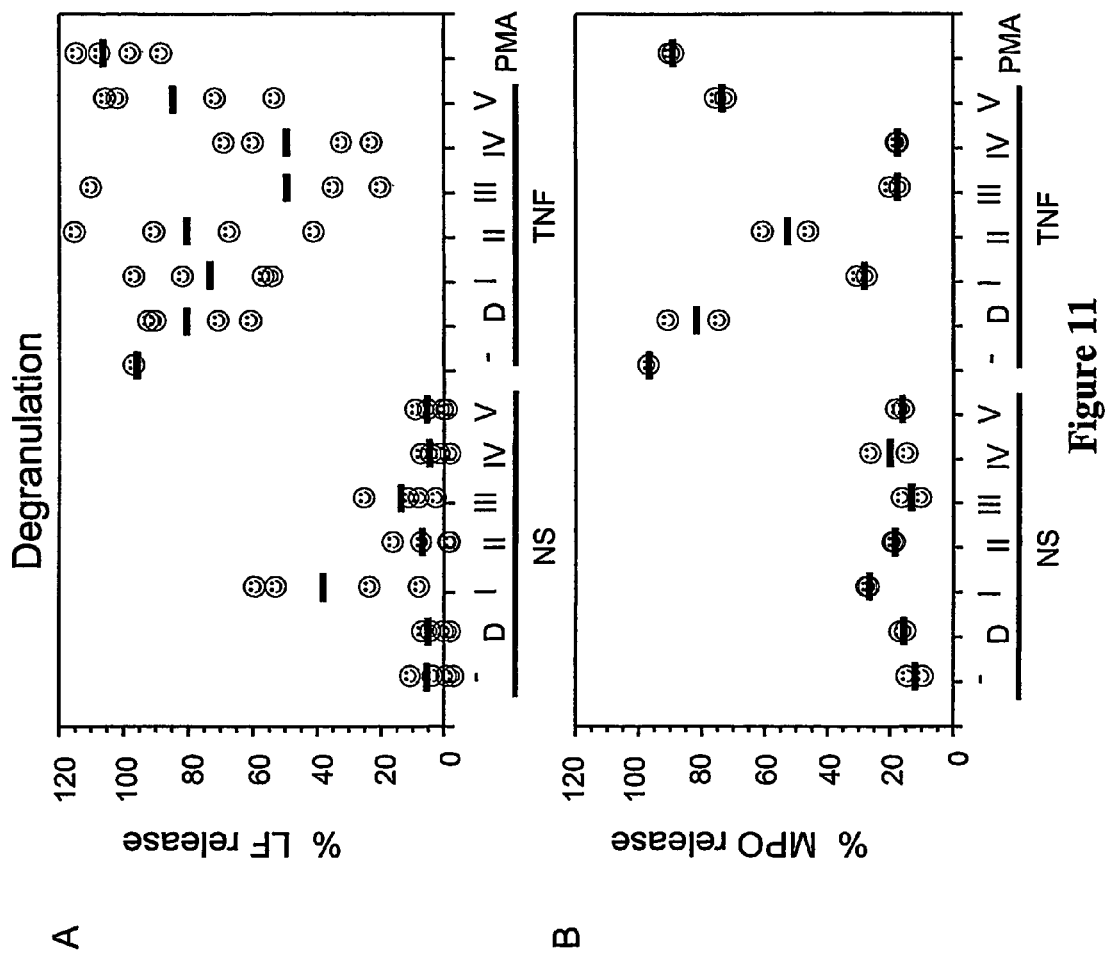
FIGS. 11A-B show the influence of Comp I-V (as described above) on the TNF triggered degranulation of neutrophils. Neutrophils were incubated with TNF, and cell supernatants were assayed for the presence of lactoferrin (LF), in FIG. 11A, and myeloperoxidase (MPO), FIG. 11B. Specific LF and MPO release are shown after normalization to that seen with TNF alone. Results are the summary of four independent experiments for LF release and two for MPO release. Each dot represents each experiment done in duplicate.

It was previously demonstrated that signals for neutrophil $H_2O_2$ release and degranulation could be regulated separately by using dominant negative form of a tyrosine kinase called Pyk2 (Han et al, "Critical Role of the Carboxyl Terminus of Proline-Rich Tyrosine Kinase (Pyk2) in the Activation of Human Neutrophils by TNF: Separation of Signals for the Respiratory Burst and Degranulation," *J. Exp. Med.* 197: 77-85(2003), which is hereby incorporated by reference in its entirety). To test whether any of these compounds has any role in degranulation, the release of lactoferrin (LF) (as a marker of specific granule) and myeloperoxidase (MPO, as a marker of azurophil granule) were measured in the supernatant. Comp II did not block the discharge of LF triggered by TNF, as shown in FIG. 11A, while Comp III and IV partially inhibited LF release. The effect of Comp I on LF release was inconclusive due to high background release of LF in non-stimulated cells. As shown in FIG. 11B, Comp II showed very moderate inhibition on MPO release, while Comp I, III, and IV exhibited almost complete inhibition. As shown in FIGS. 11A and 11B, respectively, inactive control Comp V interfered with neither LF nor MPO release elicited by TNF.

Example 6

Influence on Neutrophil Spreading and Transmigration

Figure 12A:
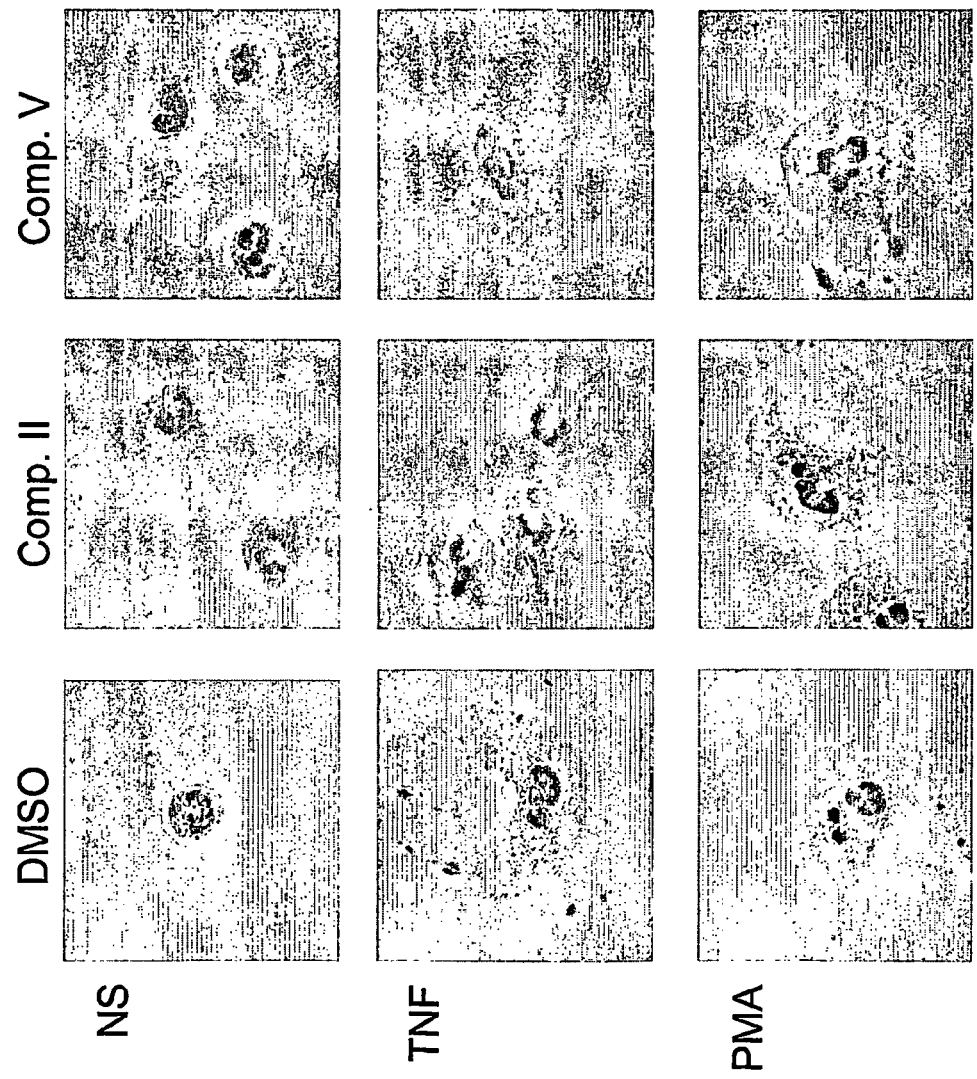
FIGS. 12A-B are photographs demonstrating the influence of Comp I-V on neutrophil spreading. Neutrophils were plated on FBS-coated glass coverslips and incubated with DMSO (D), a compound of the present invention, or a buffer (NS) at 37° C. for 30 min before stimulation with TNF (100 ng/ml), PMA (100 ng/ml), or an equal volume of KRPG, fixed, and photographed with phase-contrast microscope.
Figure 12B:
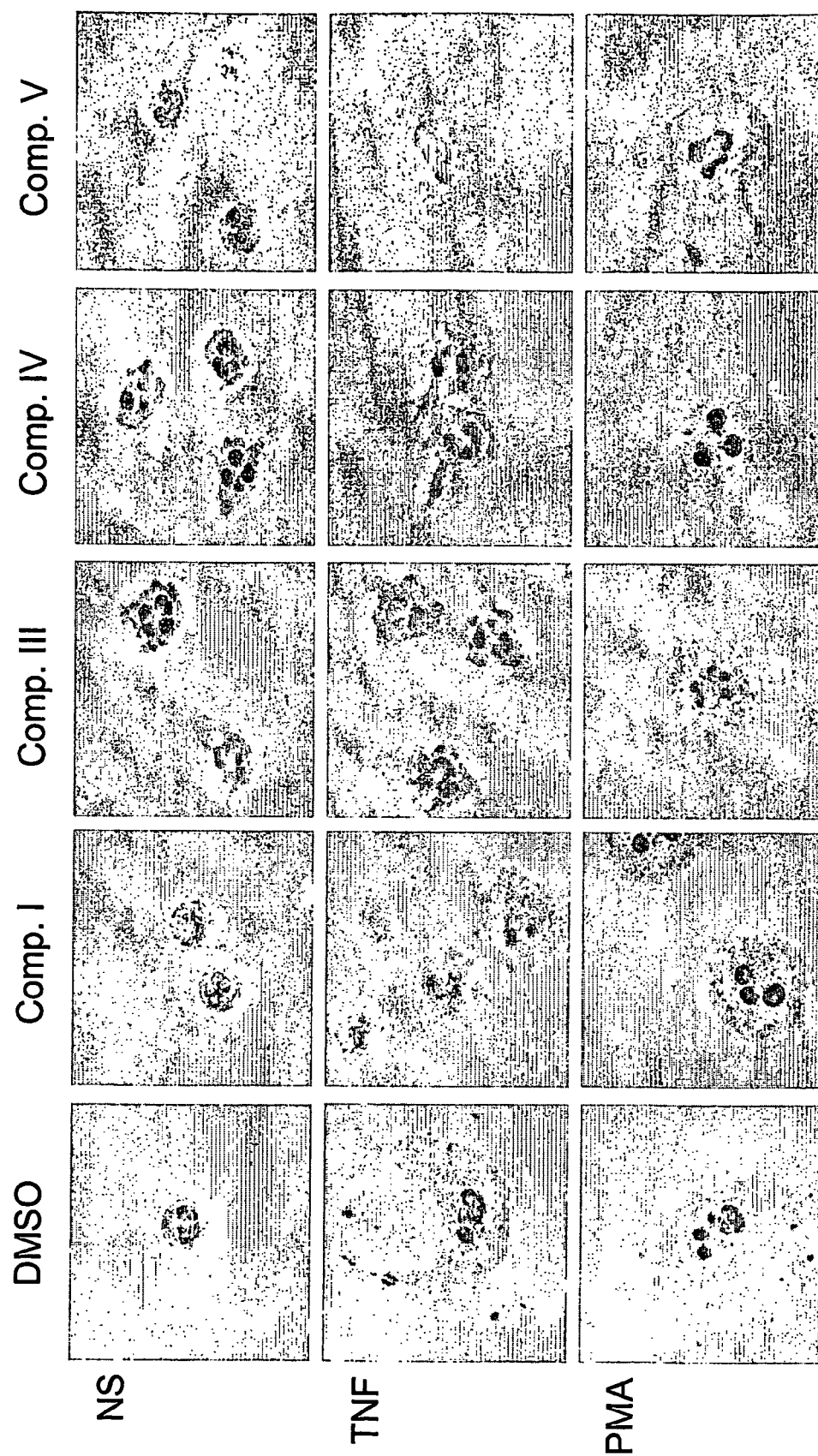

To determine whether any of these compounds are implicated in cytoskeletal rearrangement, neutrophils were treated with a compound of the present invention or DMSO and then activated with PMA or TNF. Human neutrophils, isolated as described herein above were plated on FBS-coated glass coverslips and incubated or not with a compound of the present invention at 37° C. for 30 min, followed by stimulation with TNF (100 ng/ml), PMA (100 ng/ml) or an equal volume of KRPG, fixed, and photographed with phase-contrast microscope. Neutrophils adhere and fully spread when activated. However, cells exposed to TNF after incubation with Comp I-IV were arrested in spreading. These compounds seem to block different stages of cell spreading. Comp I treated neutrophils consistently showed very heterogeneous morphology upon TNF stimulation. They display almost round and close to non-stimulated cell morphology to quite advanced, yet arrested phenotype before full spreading. Comp II and IV treated cells were arrested after flattening and extending several filopodia, as shown in FIG. 12A, and Comp III treated cells after extending a few pseudopodia, as shown in FIG. 12B. Comp III seems to block cell spreading at the earliest stage among these four compounds. None of the compounds impeded cell spreading induced by PMA. Control Comp V did not show any inhibition in cell spreading triggered by TNF nor PMA.

Example 7

Figure 13:
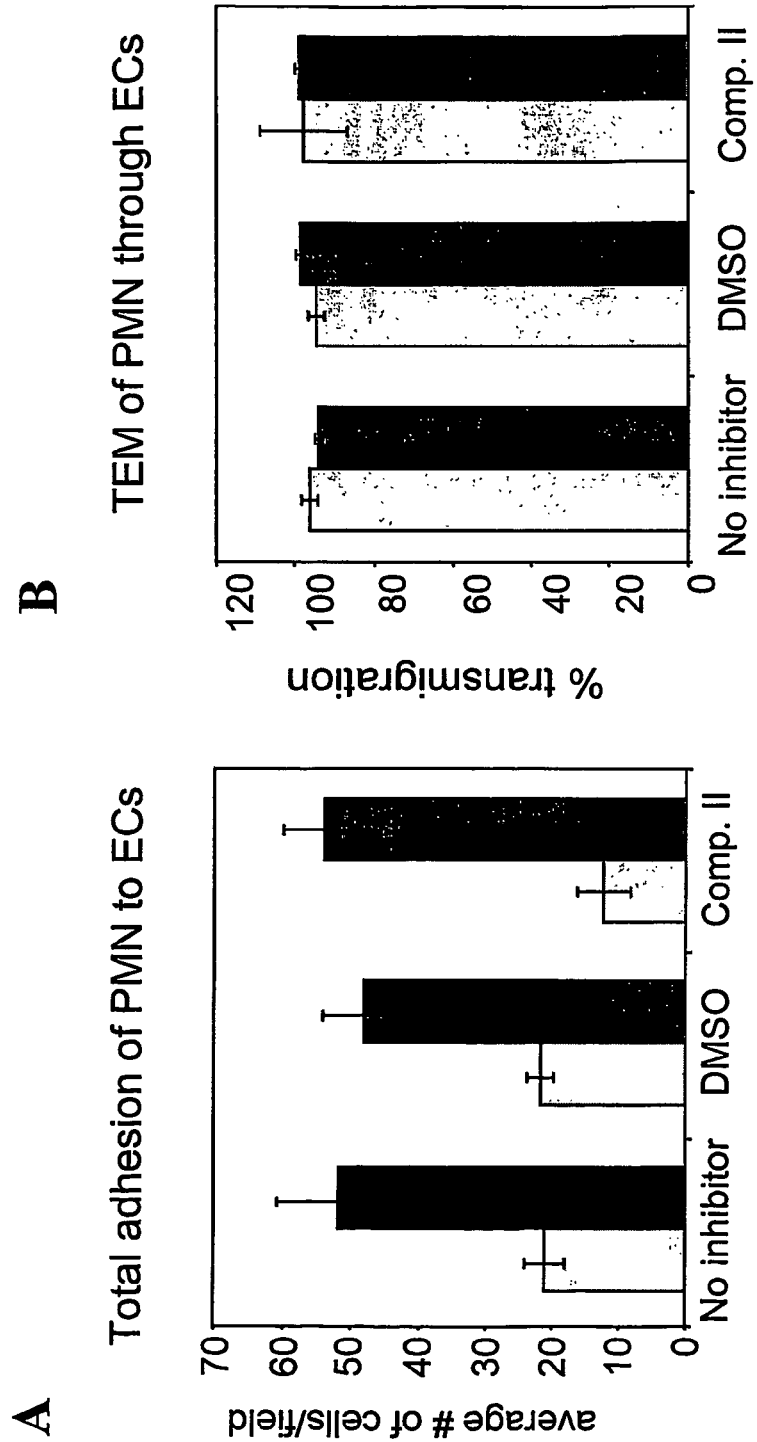
FIGS. 13A-B show the results of the transmigration of neutrophils through a TNF activated human umbilical vein endothelial cell (HUVEC) layer. Neutrophils were incubated with or without a compound of the present invention compound at RT for 30 min, layered on non-stimulated (grey bar) or TNF (50 pg/ml, black bar) stimulated HUVECs, and allowed to transmigrate at 37° C. for 30 min. Unbound cells were washed off with phosphate-buffered saline (PBS) and fixed. Cells on top of and below the HUVEC layers were stained and counted under the microscope. Results of the experiment with Comp II are shown.

Transmigration of Neutrophils Through TNF Activated Human Umbilical Vein Endothelial Cell Layers For appropriate control of invading pathogens, leukocytes must migrate to the site(s) of infection. Failure to reach the site of infection can lead to devastating outcome for the host. To test the possible blockade of transmigration to the sites of infection, neutrophils were treated with a compound of the present invention and allowed them to transmigrate through the TNF activated human umbilical vein endothelial cell (HUVEC) layer. A transendothelial migration (TEM) assay carried out and quantified as described elsewhere (Muller et al., "PECAM-1 is Required for Transendothelial Migration of Leukocytes," *J Exp Med* 178(2)449-460 (1993); Mamdouh et al., "Targeted Recycling of PECAM From Endothelial Surface-Connected Compartments During Diapedesis," *Nature* 421:748-753 (2003), which are hereby incorporated by reference in their entirety). Briefly, human umbilical vein endothelial cells (HUVEC) were isolated by standard methods (Griesmacher et al., "17 Alpha-Ethinylestradiol Decreases Production and Release of Prostacyclin in Cultured Human Umbilical Vein Endothelial Cells," *Prostaglandins* 38(4):431-8 (1989), which is hereby incorporated by reference in its entirety) and cultured in M199 medium (Gibco, Gaithersburg, Md.) supplemented with 20% normal human serum, penicillin, and streptomycin. Experiments were carried out on cells at passage two cultured on hydrated type I collagen gels in 96-well plates. In certain conditions, HUVEC were stimulated with TNF (50 pg/ml) in 5% $CO_2$ at 37° C. overnight (i.e., circa 12-18 hrs). Neutrophils were isolated from the peripheral blood of healthy adult volunteers by density gradient sedimentation in a discontinuous gradient of Ficoll (Amersham Pharmacia, Piscataway, N.J.) and Histopaque (Sigma-Aldrich, St Louis, Mo.), washed in HBSS+ 0.1% HSA, resuspended to $0.5 \times 10^6$ cells/mL and added to HUVEC monolayers. Small molecule compounds were incubated with the PMNs at RT for 30 min before TEM and allowed to remain during the duration of the assay. After PMNs were allowed to transmigrate for 30 minutes at 37° C., non-adherent PMNs were washed off with PBS and the remaining adherent and transmigrated cells were fixed with the endothelial monolayer by incubation overnight in 2.5% glutaraldehyde (Electron Microscopy Sciences, Hatfield, PA) in 0.1 sodium cacodylate buffer. HUVECs and neutrophils were differentially stained with Wright-Giemsa stain, and adherent and transmigrated cells were counted in multiple fields from the six replicates of each condition tested. Total adhesion was calculated as the total number of cells, both adherent and transmigrated, per high-powered field. The results are shown in FIGS. 13A-B. Transmigration data is expressed as the percentage of the total cells that transmigrated below the endothelial layer (% TEM). None of the compound appears to block either adhesion or transmigration of neutrophils through HUVECs, as shown in FIGS. 13A-B. Pretreatment of HUVECs with each compound before transmigration assay had no influence on the transmigration of non-treated neutrophils, indicating that none of these compounds interfere with TNF induced activation of HUVEC. Each of compounds I-IV blocked TNF elicited spreading of neutrophils, as shown in FIGS. 12A-B, yet did not interfere with the cytoskeletal rearrangement necessary for adhesion and transmigration through HUVEC. This suggests that none of these compounds are actually targeting components directly involved in cytoskeletal rearrangements. Rather, they might be interfering with the upstream events that can be bypassed when the signal is triggered through different receptors.

Example 8

Immunoprecipitation and Western Blot

Figure 14C:
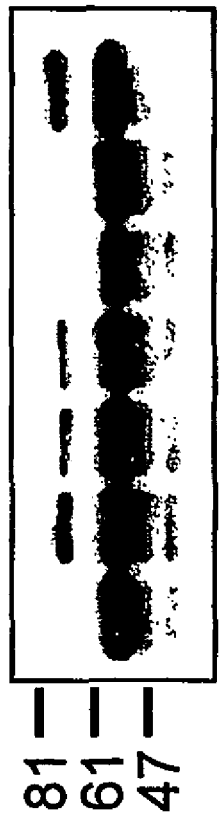
Figure 14C:
Figure 14C:
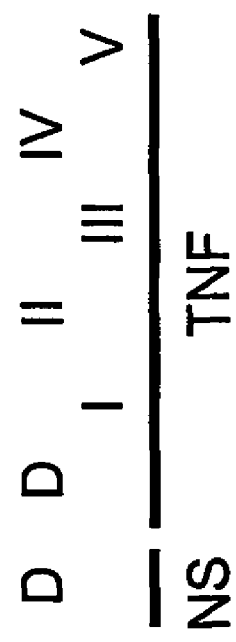
Figure 14D:
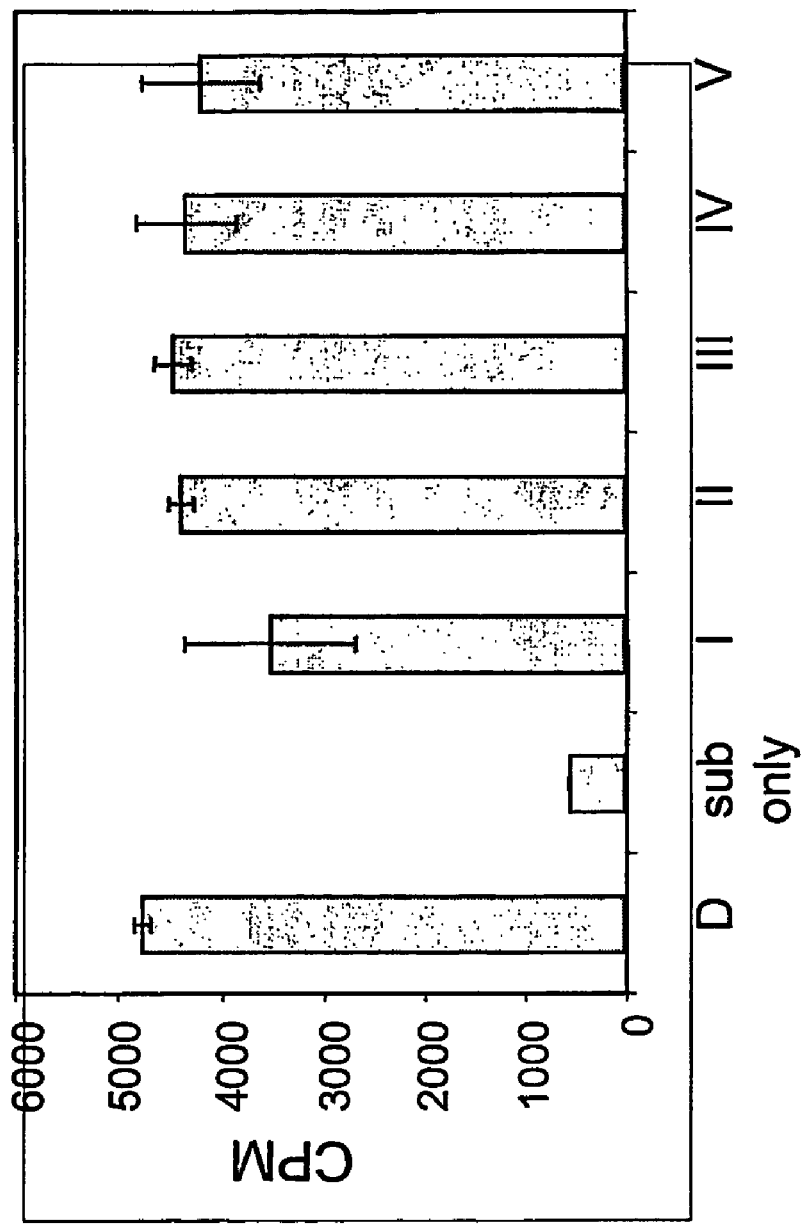

Tissue culture plates (Primaria, Falcon) were coated with 3 ml of FBS in 5% $CO_2$ at 37° C. for at least 1 h and washed twice with 0.9% saline. Isolated human neutrophils ($1.5 \times 10^6$) were added to each plate containing 4 ml of reaction mixture, incubated with each compound at 37° C. for 30 min, and stimulated with either buffer control or TNF (100 ng/ml). When cells were fully spread (20-40 min), they were treated with 5 mM diisopropylfluorophosphate to inhibit serine proteases and lysed with either 125 µl of SDS lysis buffer (10 mM Tris-HCl, pH 7.6, 150 mM NaCl, 1% SDS, 1 mM PMSF, 1 mM Na pyrophosphate, 1 mM NaF, 1 mM vanadate, 5 µg/ml each of aprotinin, leupeptin, chymostatin, pepstatin A) for western blot, or with 200 µl of non-denaturing modified RIPA buffer (10 mM Tris-HCl, pH 7.6, 150 mM NaCl, 1% Triton-X100, 1 mM PMSF, 1 mM Na pyrophosphate, 1 mM NaF, 1 mM vanadate, 5 µg/ml each of aprotinin, leupeptin, chymostatin, pepstatin A) for immunoprecipitation. The cell lysate was passed through a 26-gauge needle six times to shear DNA and centrifuged at 20,000×g for 15 min to remove cell debris and DNA. The protein concentration was determined using a Bio-Rad (Indianapolis, Ind.) kit. Cell lysates were separated by SDS-PAGE and transferred electrophoretically to nitrocellulose membranes (Schleicher & Schuell, Inc., Keene, N.H.). The membranes were incubated with 5% milk in TBST (1 M Tris-HCl, pH 7.5, 9% NaCl, 0.1% Tween-20) for 1 h at 37° C. and then overnight at 4° C. with anti-phosphotyrosine antibody (Santa Cruz), anti-Syk antibody (Transduction Laboratories, Newington, N.H.), anti-phospho-specific Pyk2 antibodies (Biosource International, Camarillo, Calif.), or anti-Pyk2 antibody (Upstate Biotech, Waltham, Mass.). Membranes were washed with TBST and incubated with secondary Ab conjugated with HRP in 5% milk in TBST for 1 h at 37° C. After further washing with TBST, bound antibody was detected by enhanced chemiluminescence (Pierce ECL, Amersham Pharmacia, Piscataway, N.J.). FIG. 14A shows the effect on TNF triggered tyrosine phosphorylation of total cellular proteins. FIG. 14B shows TNF triggered Src activity. FIG. 14C shows TNF triggered Syk activity. FIG. 14D shows TNF-induced phosphorylation of endogenous Pyk2 by Comp I-V.

Example 9

In Vitro Kinase Assay for Src and Syk

Also investigated was the impact of the compounds of the present invention on several known tyrosine kinases such as Src, Syk, and Pyk2, which are shown to be critical in the signaling pathways triggered by TNF. Kinase assays were performed according to the instructions provided by United Bioinformatica, Inc. ((UBI) Calgary, AB, Canada), from which recombinant Src and Syk were purchased. Briefly, after incubation of recombinant Src (40 U) (UBI, Calgary, AB, Canada) with each compound at RT for 30 min, Src kinase reaction buffer (100 mM Tris-HCl, pH 7.2, 125 mM $MgCl_2$, 25 mM $MnCl_2$, 2 mM EGTA, 0.25 mM $NaOV_4$, 2 mM DTT), Src kinase substrate peptide (375 μM, UBI, Calgary, AB, Canada), and [γ-32P]ATP were added to the enzyme. After incubation at 30° C. for 10 min, the reaction was stopped by addition of 40% trichloroacetic acid (TCA). Samples were transferred to a P81 paper square (UBI, Calgary, AB, Canada), the unincorporated radioactivity was washed off with 0.75% phosphoric acid and acetone, and the assay square was placed in a scintillation counter. For Syk kinase assay, reaction buffer contained 50 mM Tris-HCl, pH 7.5, 0.1 mM EGTA, 0.1 mM $NaOV_4$, 0.15 M 2-mercaptoethanol and substrate was poly (Glu-4-Tyr)(4:1) (CSI Biointernational, France). As shown in FIGS. 14B-C, none of these compounds exhibited direct inhibition on recombinant Src and Syk in vitro. However, TNF and adhesion triggered tyrosine phosphorylation of Syk was completely inhibited by Comp III and IV, while it was only moderately inhibited by Comp I and II (about 50%), as shown in FIG. 14C. It appears that these compounds block—partially by Comp I and II and completely by Comp III and IV—upstream signaling events for Syk activation rather than directly blocking Syk activity.

Figure 15:
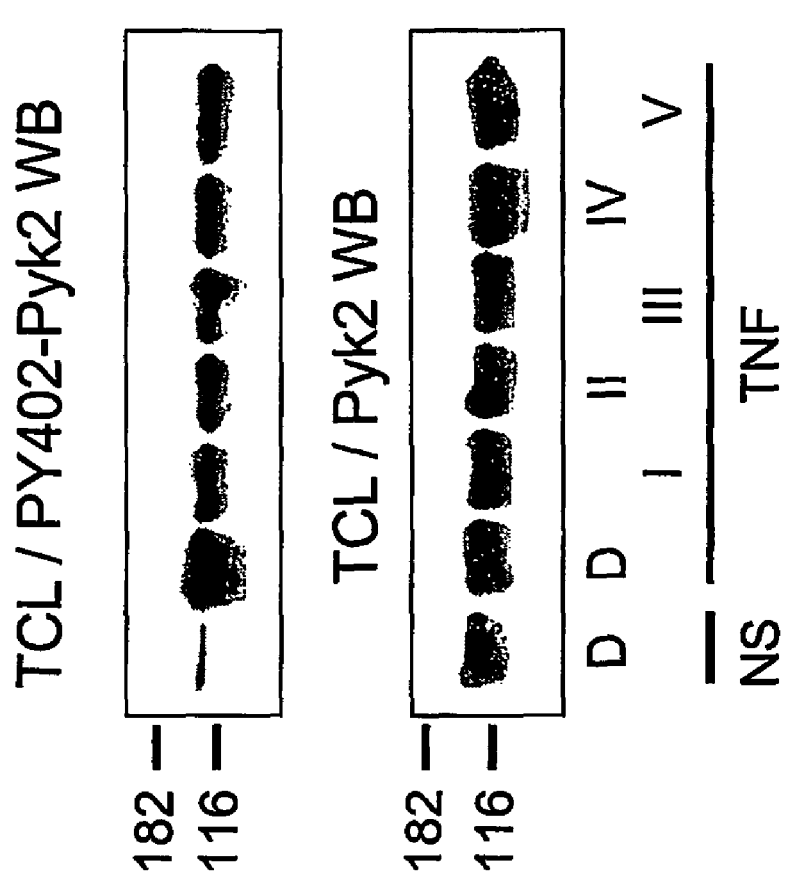
FIG. 15 shows the effect of TNF-induced phosphorylation of endogenous Pyk2. Neutrophils were treated with Comp I-V, and cell lysates prepared as indicated were western blotted (WB) with phosphorylated Pyk2 specific antibody.

The effect of each compound on the phosphorylation of tyrosine residues at 402 (Y402), which has been shown to be critical in Pyk2's kinase activity (Schlaepfer et al., "Multiple Grb2-Mediated Integrin-Stimulated Signaling Pathways to ERK2/Mitogen-Activated Protein Kinase: Summation of Both c-Src- and Focal Adhesion Kinase-Initiated Tyrosine Kinase Phosphorylation Events," *Mol Cell Biol* 18(5):2571-85 (1998), which is hereby incorporated by reference in its entirety) was investigated. TNF-induced phosphorylation of Y402 was not blocked by any of these compounds, as shown in FIG. 15. Therefore, none of these compounds seems to inhibit TNF triggered $H_2O_2$ release by directly targeting these known kinases that are essential for this pathway.

Example 10

Translocation of phox47

Figure 16:
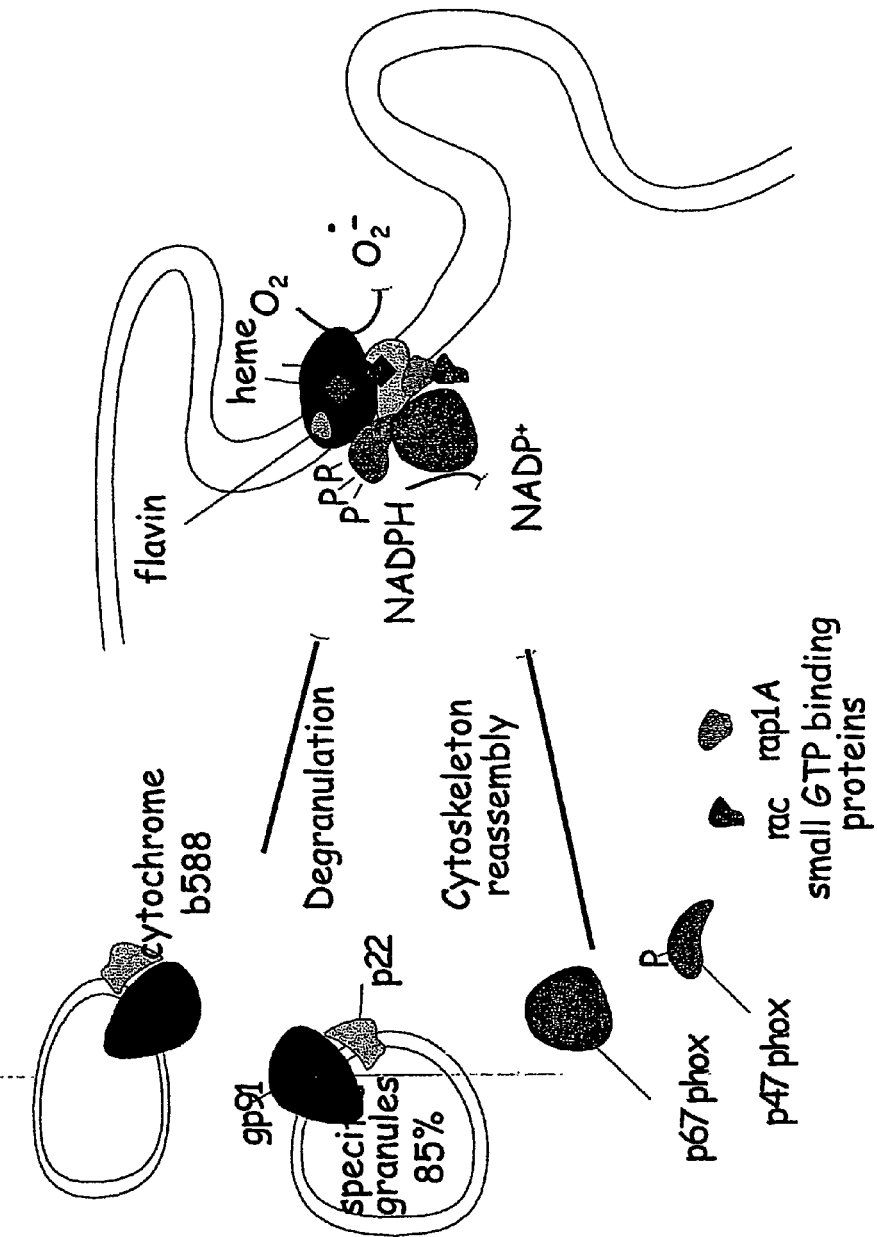
FIG. 16 is a schematic diagram of the phagocyte oxidase/NADPH oxidase (Phox) pathway.

In an attempt to identify specific steps of the biochemical pathway(s) that are influenced by Comp II, the effect on translocation of phagocyte oxidase (Phox) translocation was examined. Phox is a multi-subunit enzyme complex that generates $H_2O_2$ upon activation. Activation of Phox requires an assembly of both membrane associated and cytosolic subunits at the plasma or phagosomal membrane as well as phosphorylation of several subunits. The cytochrome b559 (also known as b558) components of phox (gp91 and gp22) are localized on the membranes of specific granules (Bjerrum et al, "Dual Granule Localization of the Dormant NADPH Oxidase and Cytochrome b559 in Human Neutrophils," *Eur J Haematol* 43(1): 67-77 (1989), which is hereby incorporated by reference in its entirety), and recruitment of these subunits to the membrane occurs simultaneously with degranulation. This pathway is shown in FIG. 16. Thus, Comp II is not likely to block $H_2O_2$ release by interfering with recruitment of the cytochrome b559 components of Phox, since degranulation takes place normally in Comp II treated cells. The influence of Comp II on the translocation of p47phox subunit, one of the components of NADPH oxidase, to the cell membrane, was examined as follows.

Figure 17:
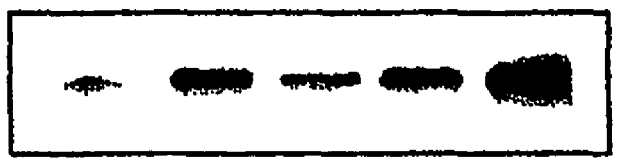
FIG. 17 shows the translocation of phox 47 subunit from the cytosol to the cell membrane. Neutrophils were incubated with DMSO or Comp II at 37° C. for 30 min and stimulated with TNF (T), PMA (P), or a buffer alone as a control (NS). After stimulation, membrane fractions were collected through ultracentrifugation, separated by SDS-PAGE and western-blotted (WB) with anti-phox 47 antibody.

Neutrophil lysates were prepared as above with 2.5% TritonX-100 lysis buffer (final concentration of 1% TritonX-100 after dilution in plate with residual KRPG). The cell lysate was passed through 26-gauge needle six times to shear DNA and centrifuged at 20,000×g for 15 min to remove cell debris and DNA. The supernatant was centrifuged again at 100,000×g for 1 h to pellet membrane fraction. The pellet was washed with PBS and resuspended in 2% TritonX-100 lysis buffer. Membrane fraction from each condition was separated by SDS-PAGE and western blotted with anti-phox 47 antibody. As shown in FIG. 17, activation triggered translocation of phox 47 was not inhibited by Comp II. The behavior of Comp II is reminiscent of dominant negative Pyk2 (Han et al, "Critical Role of the Carboxyl Terminus of Proline-Rich Tyrosine Kinase (Pyk2) in the Activation of Human Neutrophils by TNF: Separation of Signals for the Respiratory Burst and Degranulation," *J. Exp. Med.* 197: 77-85(2003), which is hereby incorporated by reference in its entirety) in that it inhibited TNF elicited RB and cell spreading while sparing degranulation and bacterial killing ability of PMNs. Yet, Comp II did not block TNF and adhesion triggered activation of Syk or Pyk2 in PMNs.

Although the invention has been described in detail for the purposes of illustration, it is understood that such detail is solely for that purpose, and variations can be made therein by those skilled in the art without departing from the spirit and scope of the invention which is defined by the following claims.

What is claimed:
1. A method of inhibiting respiratory burst in adherent neutrophils without inhibiting degranulation in neutrophils or bacterial killing by neutrophils, said method comprising:
   contacting adherent neutrophils with an effective amount of a chemical compound, wherein the compound has the formula:

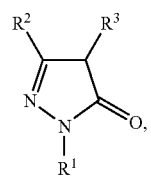

wherein:
   $R^1$ is substituted or unsubstituted phenyl;
   $R^2$ is $C_1$-$C_4$ alkyl; and
   $R^3$ is substituted or unsubstituted quinoline with or without a linking group.

2. The method according to claim 1, wherein the compound has the formula:

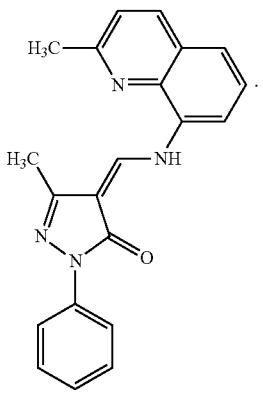

3. A method of inhibiting respiratory burst in adherent neutrophils without inhibiting degranulation in neutrophils or bacterial killing by neutrophils, said method comprising:
    contacting adherent neutrophils with an effective amount of a chemical compound, wherein the compound has the formula:

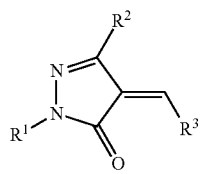

wherein:
    $R^1$ is substituted or unsubstituted phenyl;
    $R^2$ is $C_1$-$C_4$ alkyl; and
    $R^3$ is substituted or unsubstituted benzoylhydrazino.

4. The method according to claim 3, wherein the compound has the formula:

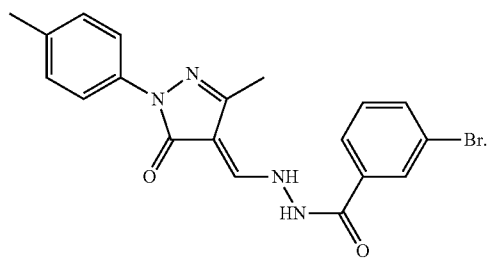

5. The method according to claim 3, wherein the compound has the formula:

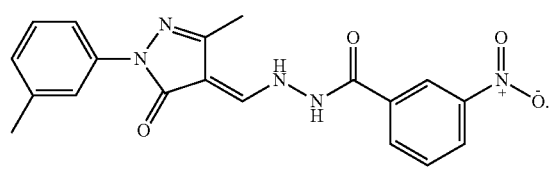

6. The method according to claim 3, wherein the compound has the formula:

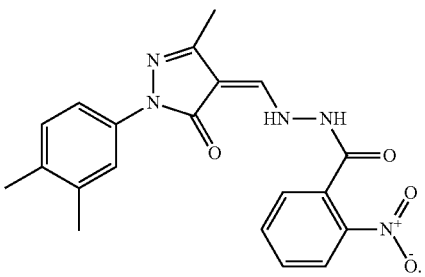

7. The method according to claim 3, wherein the compound has the formula:

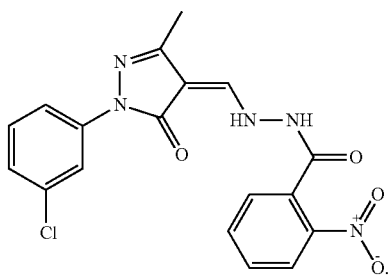

8. The method according to claim 3, wherein the compound has the formula:

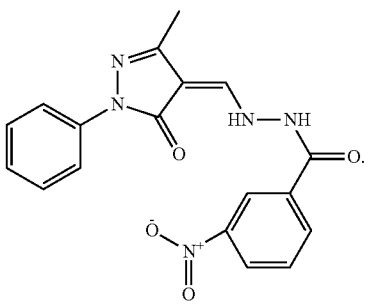

9. The method according to claim 3, wherein the compound has the formula:

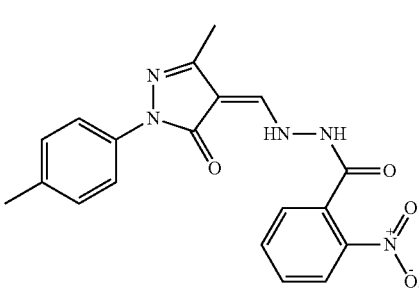

10. The method according to claim 3, wherein the compound has the formula:

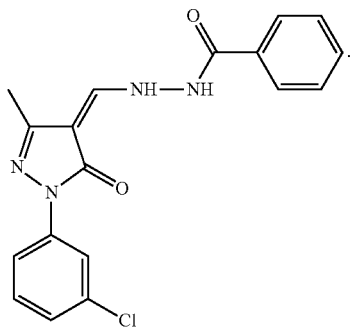

11. The method according to claim 1, wherein said contacting neutrophils is carried out in vitro.

12. The method according to claim 1, wherein said contacting neutrophils is carried out in vivo.

13. The method according to claim 1, wherein said contacting with a compound inhibits respiratory burst in adherent neutrophils triggered by an agent selected from the group consisting of a chemokine, a cytokine, bacteria, and a bacterial factor.

14. The method according to claim 13, wherein said contacting with a compound inhibits respiratory burst in adherent neutrophils triggered by a chemokine selected from the group consisting of macrophage inflammatory protein-1 (MIP-1), interleukin-8 (IL-8), and chemoattractant complement component C5a.

15. The method according to claim 13, wherein said contacting with a compound inhibits respiratory burst in adherent neutrophils triggered by a cytokine selected from the group consisting of tumor necrosis factor (TNF), lymphotoxin, granulocyte-specific colony stimulating factor (G-CSF), and granulocyte/macrophage-specific colony stimulating factor (GM-CSF).

16. The method according to claim 13, wherein said contacting with a compound inhibits respiratory burst in adherent neutrophils triggered by bacteria selected from the group consisting of whole bacteria, bacterial cell wall components, and secreted or shed bacterial products.

17. The method according to claim 13, wherein said contacting with a compound inhibits respiratory burst in adherent neutrophils triggered by a bacterial factor that is a soluble bacterial complement protein.

18. The method according to claim 3, wherein said contacting neutrophils is carried out in vitro.

19. The method according to claim 3, wherein said contacting neutrophils is carried out in vivo.

20. The method according to claim 3, wherein said contacting with a compound inhibits respiratory burst in adherent neutrophils triggered by an agent selected from the group consisting of a chemokine, a cytokine, bacteria, and a bacterial factor.

21. The method according to claim 20, wherein said contacting with a compound inhibits respiratory burst in adherent neutrophils triggered by a chemokine selected from the group consisting of macrophage inflammatory protein-1 (MIP-1), interleukin-8 (IL-8), and chemoattractant complement component C5a.

22. The method according to claim 20, wherein said contacting with a compound inhibits respiratory burst in adherent neutrophils triggered by a cytokine selected from the group consisting of tumor necrosis factor (TNF), lymphotoxin, granulocyte-specific colony stimulating factor (G-CSF), and granulocyte/macrophage-specific colony stimulating factor (GM-CSF).

23. The method according to claim 20, wherein said contacting with a compound inhibits respiratory burst in adherent neutrophils triggered by bacteria selected from the group consisting of whole bacteria, bacterial cell wall components, and secreted or shed bacterial products.

24. The method according to claim 20, wherein said contacting with a compound inhibits respiratory burst in adherent neutrophils triggered by a bacterial factor that is a soluble bacterial complement protein.

* * * * *